(12) United States Patent
Collas et al.

(10) Patent No.: US 7,253,334 B2
(45) Date of Patent: Aug. 7, 2007

(54) METHODS FOR CLONING NON-HUMAN MAMMALS USING REPROGRAMMED DONOR CHROMATIN OR DONOR CELLS

(75) Inventors: Philippe Collas, Oslo (NO); James M. Robl, Belchertown, MA (US); Eddie Sullivan, Manhattan, KS (US); Poothappillai Kasinathan, Brandon, SD (US)

(73) Assignee: Aurox, LLC, Westport, CT (US)

( * ) Notice: Subject to any disclaimer, the term of this patent is extended or adjusted under 35 U.S.C. 154(b) by 404 days.

(21) Appl. No.: 10/032,191

(22) Filed: Dec. 21, 2001

(65) Prior Publication Data

US 2003/0046722 A1    Mar. 6, 2003

(51) Int. Cl.
*C12N 15/00* (2006.01)
*G01N 33/00* (2006.01)
*C12P 21/00* (2006.01)
*A01K 67/00* (2006.01)

(52) U.S. Cl. .................... 800/24; 800/3; 800/4; 800/8; 800/21; 800/25; 435/325

(58) Field of Classification Search ............ 800/3, 800/4, 8, 21, 24, 25; 435/325, 440
See application file for complete search history.

(56) References Cited

U.S. PATENT DOCUMENTS

| | | | |
|---|---|---|---|
| 4,873,316 A | 10/1989 | Meade et al. ............... 530/412 |
| 4,959,317 A | 9/1990 | Sauer ...................... 435/172.3 |
| 4,994,384 A | 2/1991 | Prather et al. ............ 435/172.2 |
| 5,057,420 A | 10/1991 | Massey ................... 435/172.2 |
| 5,096,822 A | 3/1992 | Rosenkrans, Jr. et al. ........................ 435/240.1 |
| 5,160,312 A | 11/1992 | Voelkel ........................ 600/34 |
| 5,175,384 A | 12/1992 | Krimpenfort et al. .......... 800/2 |
| 5,213,979 A | 5/1993 | First et al. ................ 435/240.2 |
| 5,240,840 A | 8/1993 | Feinberg et al. ......... 435/172.3 |
| 5,434,066 A | 7/1995 | Bebee et al. ............. 435/172.3 |
| 5,434,340 A | 7/1995 | Krimpenfort et al. .......... 800/2 |
| 5,453,366 A | 9/1995 | Sims et al. .............. 435/172.3 |
| 5,464,764 A | 11/1995 | Capecchi et al. ......... 435/172.3 |
| 5,470,560 A | 11/1995 | Martin, Jr. ................... 424/9.2 |
| 5,480,772 A | 1/1996 | Wangh .......................... 435/2 |
| 5,482,856 A | 1/1996 | Fell, Jr. et al. .......... 435/320.1 |
| 5,487,992 A | 1/1996 | Capecchi et al. ......... 435/172.3 |
| 5,496,720 A | 3/1996 | Susko-Parrish et al. .. 435/240.2 |
| 5,527,674 A | 6/1996 | Guerra et al. ................... 435/6 |
| 5,545,806 A | 8/1996 | Lonberg et al. ................ 800/2 |
| 5,545,807 A | 8/1996 | Surani et al. ................... 800/2 |
| 5,565,350 A | 10/1996 | Kmiec ..................... 435/172.3 |
| 5,565,362 A | 10/1996 | Rosen ...................... 435/320.1 |
| 5,569,825 A | 10/1996 | Lonberg et al. ................ 800/2 |
| 5,583,016 A | 12/1996 | Villeponteau et al. ..... 435/91.3 |
| 5,591,669 A | 1/1997 | Krimpenfort et al. .......... 800/2 |
| 5,612,205 A | 3/1997 | Kay et al. ................ 435/172.3 |
| 5,614,396 A | 3/1997 | Bradley et al. ........... 435/172.3 |
| 5,625,126 A | 4/1997 | Lonberg et al. ................ 800/2 |
| 5,627,059 A | 5/1997 | Capecchi et al. ......... 435/172.3 |
| 5,631,153 A | 5/1997 | Capecchi et al. ......... 435/172.3 |
| 5,633,076 A | 5/1997 | DeBoer et al. ........... 435/172.3 |
| 5,633,425 A | 5/1997 | Lonberg et al. ................ 800/2 |
| 5,639,457 A | 6/1997 | Brem et al. ............... 424/184.1 |
| 5,651,992 A | 7/1997 | Wangh ........................ 424/520 |
| 5,654,182 A | 8/1997 | Wahl et al. ............... 435/172.1 |
| 5,654,183 A | 8/1997 | Anderson et al. ......... 435/172.3 |
| 5,661,016 A | 8/1997 | Lonberg et al. .......... 435/172.3 |
| 5,677,177 A | 10/1997 | Wahl et al. ................. 435/325 |
| 5,679,523 A | 10/1997 | Li et al. ........................ 435/6 |
| 5,695,977 A | 12/1997 | Jurka ...................... 435/172.3 |
| 5,698,763 A | 12/1997 | Weissmann et al. ........... 800/2 |
| 5,721,367 A | 2/1998 | Kay et al. ...................... 800/2 |
| 5,733,730 A | 3/1998 | De Lange ...................... 435/6 |
| 5,741,957 A | 4/1998 | Deboer et al. ................. 800/2 |
| 5,750,172 A | 5/1998 | Meade et al. ............... 426/580 |
| 5,756,325 A | 5/1998 | Kmiec ..................... 435/172.3 |
| 5,763,240 A | 6/1998 | Zarling et al. ........... 435/172.3 |
| 5,770,422 A | 6/1998 | Collins ..................... 435/194 |
| 5,770,429 A | 6/1998 | Lonberg et al. .......... 435/240.2 |
| 5,773,217 A | 6/1998 | Wangh .......................... 435/6 |
| 5,776,744 A | 7/1998 | Glazer et al. ............ 435/172.3 |
| 5,780,296 A | 7/1998 | Holloman et al. ........ 435/320.1 |
| 5,786,217 A | 7/1998 | Tubo et al. ................. 435/402 |
| 5,789,215 A | 8/1998 | Berns et al. ............. 435/172.3 |
| 5,789,650 A | 8/1998 | Lonberg et al. ................ 800/2 |
| 5,801,030 A | 9/1998 | McVey et al. ........... 435/172.3 |
| 5,814,318 A | 9/1998 | Lonberg et al. .......... 424/184.1 |
| 5,821,117 A | 10/1998 | Sandrin et al. .......... 435/320.1 |

(Continued)

FOREIGN PATENT DOCUMENTS

| | | |
|---|---|---|
| EP | 0546073 | 9/1997 |
| EP | 1106061 | 6/2001 |
| WO | WO 90/06359 | 6/1990 |
| WO | WO 91/08216 | 6/1991 |

(Continued)

OTHER PUBLICATIONS

Simerly et al. Science (2003) 300:297.*
Mitalipov et al. Biol Reprod (2002) 66:1367-1373.*
Collas et al., "Electrical Activation of Mouse Oocytes," Theriogenology 32/5:835-844 (1989).
Collas et al., "Electrically Induced Calcium Elevation, Activation, and Parthenogenetic Development of Bovine Oocytes," Molecular Reproduction and Development 34:212-223 (1993).

(Continued)

*Primary Examiner*—Joseph Woitach
(74) *Attorney, Agent, or Firm*—Clark & Elbing LLP

(57) ABSTRACT

The invention provides methods for cloning mammals that allow the donor chromosomes or donor cells to be reprogrammed prior to insertion into an enucleated oocyte. The invention also features methods of inserting chromosomes or nuclei into recipient cells.

24 Claims, 9 Drawing Sheets

U.S. PATENT DOCUMENTS

| | | | | |
|---|---|---|---|---|
| 5,827,690 | A | 10/1998 | Meade et al. | 435/69.6 |
| 5,830,698 | A | 11/1998 | Reff et al. | 435/69.1 |
| 5,837,857 | A | 11/1998 | Villeponteau et al. | 536/24.31 |
| 5,843,643 | A | 12/1998 | Ratner | 435/6 |
| 5,843,754 | A | 12/1998 | Susko-Parrish et al. | 435/240 |
| 5,849,992 | A | 12/1998 | Meade et al. | 800/2 |
| 5,874,299 | A | 2/1999 | Lonberg et al. | 435/320.1 |
| 5,876,979 | A | 3/1999 | Andrews et al. | 435/91.3 |
| 5,877,397 | A | 3/1999 | Lonberg et al. | 800/2 |
| 5,905,042 | A | 5/1999 | Stice et al. | 435/373 |
| 5,945,577 | A | 8/1999 | Stice et al. | 800/24 |
| 5,952,222 | A | 9/1999 | Rosenkrans, Jr. et al. | 435/325 |
| 6,001,654 | A | 12/1999 | Anderson et al. | 435/377 |
| 6,011,197 | A | 1/2000 | Strelchenko et al. | 800/24 |
| 6,023,010 | A | 2/2000 | Krimpenfort et al. | 800/2 |
| 6,077,710 | A | 6/2000 | Susko-Parrish et al. | 435/375 |
| 6,107,543 | A | 8/2000 | Sims et al. | 800/21 |
| 6,147,276 | A | 11/2000 | Campbell et al. | 800/24 |
| 6,153,428 | A | 11/2000 | Gustafsson et al. | 435/325 |
| 6,194,202 | B1 | 2/2001 | Susko-Parrish et al. | 435/325 |
| 6,204,061 | B1 | 3/2001 | Capecchi et al. | 435/463 |
| 6,211,429 | B1* | 4/2001 | Machaty et al. | 800/24 |
| 6,215,041 | B1 | 4/2001 | Stice et al. | 800/24 |
| 6,235,969 | B1 | 5/2001 | Stice et al. | 800/24 |
| 6,245,567 | B1 | 6/2001 | Wangh | 435/408 |
| 6,252,133 | B1 | 6/2001 | Campbell et al. | 800/24 |
| 6,258,998 | B1 | 7/2001 | Damiani et al. | 800/24 |
| 6,271,436 | B1 | 8/2001 | Piedrahita et al. | 800/21 |
| 6,300,129 | B1 | 10/2001 | Lonberg et al. | 435/326 |
| 6,753,457 | B2 | 6/2004 | Wangh | 800/24 |
| 2001/0037513 | A1 | 11/2001 | Yang et al. | 800/21 |
| 2001/0039667 | A1 | 11/2001 | Stice et al. | 800/15 |
| 2001/0044937 | A1 | 11/2001 | Schatten et al. | 800/21 |
| 2001/0053550 | A1 | 12/2001 | Stice | 435/455 |
| 2002/0001842 | A1* | 1/2002 | Chapman | 435/449 |
| 2002/0010949 | A1 | 1/2002 | Stice et al. | 800/24 |
| 2002/0012655 | A1 | 1/2002 | Stice et al. | 424/93.2 |
| 2002/0012660 | A1 | 1/2002 | Colman et al. | 424/93.21 |
| 2002/0019993 | A1 | 2/2002 | Wakayama, Jr. | 800/21 |
| 2002/0056149 | A1 | 5/2002 | Campbell et al. | 800/14 |
| 2002/0094968 | A1 | 7/2002 | Wolffe et al. | 514/44 |
| 2002/0112254 | A1 | 8/2002 | Campbell et al. | 800/14 |
| 2002/0124277 | A1 | 9/2002 | Campbell et al. | 800/14 |
| 2002/0129394 | A1 | 9/2002 | Aso et al. | 800/15 |
| 2002/0142397 | A1 | 10/2002 | Collas et al. | |
| 2003/0037347 | A1 | 2/2003 | Robi et al. | 800/6 |
| 2003/0037352 | A1 | 2/2003 | Campbell et al. | 800/14 |
| 2003/0046722 | A1 | 3/2003 | Collas et al. | 800/21 |
| 2004/0068760 | A1 | 4/2004 | Robi et al. | 800/6 |
| 2004/0072288 | A1 | 4/2004 | Collas et al. | 435/69.1 |
| 2005/0014258 | A1 | 1/2005 | Collas et al. | |

FOREIGN PATENT DOCUMENTS

| | | |
|---|---|---|
| WO | WO 92/03917 | 3/1992 |
| WO | WO 93/04169 | 3/1993 |
| WO | WO 93/12227 | 6/1993 |
| WO | WO 93/25567 | 12/1993 |
| WO | WO 94/21799 | 9/1994 |
| WO | WO 94/25585 | 11/1994 |
| WO | WO 95/20661 | 8/1995 |
| WO | WO 95/28412 | 10/1995 |
| WO | WO 95/33828 | 12/1995 |
| WO | WO 97/07668 | 3/1997 |
| WO | WO 97/07669 | 3/1997 |
| WO | WO 97/12035 | 4/1997 |
| WO | WO 98/14593 | 4/1998 |
| WO | WO 98/30683 | 7/1998 |
| WO | WO 98/33387 | 8/1998 |
| WO | WO 98/37183 | 8/1998 |
| WO | WO 98/39416 | 9/1998 |
| WO | WO 99/21415 | 5/1999 |
| WO | WO 1999/34669 | 7/1999 |
| WO | WO 99/45962 | 9/1999 |
| WO | WO 99/60108 | 11/1999 |
| WO | WO 00/25578 | 5/2000 |
| WO | WO 00/42174 | 7/2000 |
| WO | WO 00/51424 | 9/2000 |
| WO | WO 00/67568 | 11/2000 |
| WO | WO 00/67569 | 11/2000 |
| WO | WO 00/74477 | 12/2000 |
| WO | WO 01/00809 | 1/2001 |
| WO | WO 01/23541 | 4/2001 |
| WO | WO 01/30992 | 5/2001 |
| WO | WO 01/35735 | 5/2001 |
| WO | WO 02/14469 | 2/2002 |
| WO | WO 2002/24872 | 3/2002 |
| WO | WO 2002/057415 | 7/2002 |
| WO | WO 02/067665 | 9/2002 |
| WO | WO 03/064618 | 8/2003 |
| WO | WO 2004/094611 A2 | 11/2004 |
| WO | WO 2005/049788 | 6/2005 |

OTHER PUBLICATIONS

Fissore et al., "Intracellular $Ca^{2+}$ Response of Rabbit Oocytes to Electrical Stimulation." Molecular Reproduction and Development 32: 9-16 (1992).

Shi et al., "Synergistic Effect of A23187 and Cycloheximide Allows Effective Activation of Freshly Matured Bovine Oocytes," Theriogenology 39:309 (1993).

Wright and Bondioli, "Aspects of *In Vitro* Fertilization and Embryo Culture in Domestic Animals," J. Anim. Sci. 53:702 (1981).

Yang et al., "Improved Activation by Combined Cycloheximide and Electric Pulse Treatment of Bovine Follicular Oocytes Matured in Vitro for 23-24 Hours," Biol. Reprod. 46:117 (Abstract 268) (1992).

U.S. Appl. No. 09/650,194.

U.S. Appl. No. 09/357,445.

Commonwealth of Massachusetts Superior Court Civil Action No. 04-0445 BLS2 (2004).

United States District Court, District of Massachusetts, Civil Action No. 04-11013-RGS (2004).

Collas et al., "Reprogrammed Gene Expression in a Somatic Cell-Free Extract," *Transgenic Research* 11:75 (Abstract) (2002).

Coppock et al., "Replication of *Xenopus* Erythrocyte Nuclei in a Homologous Egg Extract Requires Prior Proteolytic Treatment," *Developmental Biology* 131:102-110 (1989).

Dimitrov et al., "Remodeling Somatic Nuclei in *Xenopus laevis* egg extracts: Molecular Mechanisms for the Selective Release of Histones H1 and H1o from Chromatin and the Acquisition of Transcriptional Competence," *The EMBO Journal* 15:5897-5906 (1996).

Huang et al., "The Enhancement of Specific Gene Transcriptionin Isolated Nuclei by Added HeLa Whole Cell Extract," *Int. J. Biochem.* 16:963-969 (1984).

Collas, "Nuclear Envelope Disassembly in Mitotic Extract Requires Functional Nuclear Pores and a Nuclear Lamina," *Journal of Cell Science* 111:1293-1303 (1998).

Collas, "Modulation of Plasmid DNA Methylation and Expression in Zebrafish Embryos," *Nucleic Acids Research* 26:4454-4461 (1998).

Martins et al., "HA95 is a Protein of the Chromatin and Nuclear Matrix Regulating Nuclear Envelope Dynamics," *Journal of Cell Science* 113:3703-3713 (2000).

Weiss et al., "DNA Demethylation in Vitro: Involvement of RNA," *Cell* 86:709-718 (1996).

University of Massachusetts, Uniform Invention Disclosure Form dated Jul. 7, 2000.

University of Massachusetts, Uniform Invention Disclosure Form dated Nov. 23, 1998.

U.S. Appl. No. 60/425,056, filed Nov. 8, 2002.

U.S. Appl. No. 60/464,227.

U.S. Appl. No. 60/506,901, filed Sep. 26, 2003.

U.S. Utility Appl. No. 10/705,519, filed Nov. 10, 2003.

U.S. Continuation Appl. No. 11/011,711, filed Dec. 14, 2004.
Amano et al., "Full-Term Development of Enucleated Mouse Oocytes Fused with Embryonic Stem Cells from Different Cell Lines," *Reproduction* 121:729-733 (2001).
Annas et al., "Stem Cell Politics, Ethics and Medical Progress," *Nat. Med.* 5:1339-1341 (1999).
Bell et al., "The Analysis of Costimulatory Receptor Signaling Cascades in Normal T Lymphocytes Using *In Vitro* Gene Transfer and Reporter Gene Analysis," *Nat. Med.* 7:1155-1158 (2001).
Blau et al., "Plasticity of Cell Fate: Insights from Heterokaryons," *Seminars in Cell & Dev. Biol.* 10:267-272 (1999).
Burke et al., "A Cell Free System to Study Reassembly of the Nuclear Envelope at the End of Mitosis," *Cell* 44:639-652 (1986).
Campbell et al., "Totipotency of Multipotentiality of Cultured Cells: Applications and Progress," *Theriogenology* 47:63-72 (1997).
Cheong et al., "Relationship Between Nuclear Remodeling and Subsequent Development of Mouse Embryonic Nuclei Transferred to Enucleated Oocytes," *Molecular Reproduction and Development* 37:138-145 (1994).
Church, "Are Problems Posed by Genetically Engineered Animals?," *Applied Animal Behavior Science* 20:73-82 (1988).
Cibelli et al., "Bovine Chimeric Offspring Produced by Transgenic Embryonic Stem Cells Generated from Somatic Cell Nuclear Transfer Embryos," *Theriogenology* p. 236.
Cibelli et al., "Transgenic Bovine Chimeric Offspring Produced from Somatic Cell-Derived Stem-Like Cells," *Nat. Biotechnol.* 16:642-646 (1998).
Collas et al., "Lipophilic Organizing Structures of Sperm Nuclei Target Membrane Vesicle Binding and Are Incorporated into the Nuclear Envelope," *Dev. Biol.* 169:123-135 (1995).
Collas, "Sequential PKC- and Cdc2-Mediated Phosphorylation Events Elicit Zebrafish Nuclear Envelope Disassembly," *J. Cell Sci.* 112:977-987 (1999).
Collas et al., "Sorting Nuclear Membrane Proteins at Mitosis," *Trends in Cell Biol.* 10:5-8 (2000).
Collas et al., "The A-Kinase Anchoring Protein, AKAP95, Is A Multivalent Protein with a Key Role in Chromatin Condensation at Mitosis," *J. Cell Biol.* 147:1167-1179 (1999).
Collas et al., "Relationship Between Nuclear Remodeling and Development in Nuclear Transplant Rabbit Embryos," *Biol. Reprod.* 45:455-465 (1991).
Condorelli et al., "Cardiomyocytes Induce Endothelial Cells to Transdifferentiate into Cardiac Muscle: Implications for Myocardium Regeneration," *Proc. Natl. Acad. Sci. U.S.A.* 98:10733-10738 (2001).
Costa et al., "Comparative Analysis of Three Genetic Modifications Designed to Inhibit Human Serum-mediated Cytolysis," *Xenotransplantation* 6:6-16 (1999).
Cubizolles et al., "pEg7, A New *Xenopus* Protein Required for Mitotic Chromosome Condensation in Egg Extracts," *J. Cell Biol.* 143:1437-1446 (1998).
de Anta et al., "k-FGF Protoncogene Expression Is Associated with Murine Testicular Teratogenesis, But Is Not Involved During Mouse Testicular Development," *Histol. Histopathol.*, 11:33-41 (1996).
DiBerardino et al., "Feeding Tadpoles Cloned from *Rana* Erythrocyte Nuclei," *Proc. Natl. Acad. Sci. U.S.A.*, 83:8231-8234 (1986).
Eggan et al., "Hybrid Vigor, Fetal Overgrowth, and Viability of Mice Derived by Nuclear Cloning and Tetraploid Embryo Complementation," *Proc. Natl. Acad Sci U.S.A.* 98:6209-6214 (2001).
Evans et al, "Mitochondrial DNA Genotypes in Nuclear Transfer-Derived Cloned Sheep," *Nat. Genet.* 23:90-93 (1999).
Finlay et al., "Inhibition of In Vitro Nuclear Transport by a Lectin that Binds to Nuclear Pores," *J. Cell Biol.* 104:189-200 (1987).
Finlay et al., "Reconstitution of Biochemically Altered Nuclear Pores: Transport can be Eliminated and Restored," *Cell* 60:17-29 (1990).
Fuchs et al., "Stem Cells: a New Lease on Life," *Cell* 100:143-155 (2000).
Funderburgh et al., "Proteoglycan Expression During Transforming Growth Factor β-Induced Keratocyte-Myofibroblast Transdifferentiation," *J. Biol. Chem.* 276:44173-44178 (2001).

Gjertsen et al., "Cytotoxic $CD4^+$ And $CD8^+$ T Lymphocytes, Generated By Mutant p21-*ras* (12Val) Peptide Vaccination of a Patient, Recognize 12Val-Dependent Nested Epitopes Present Within the Vaccine Peptide and Kill Autologous Tumour Cells Carrying this Mutation," *Int. J. Cancer* 72:784-790 (1997).
Görlich et al., "Identification of Different Roles for RanGDP and RanGTP in Nuclear Protein Import," *EMBO J.* 15:5584-5594 (1996).
Görlich et al., "A Novel Class of RanGTP Binding Proteins," *J. Cell Biol.* 138:65-80 (1997).
Greiner et al., "SCID Mouse Models of Human Stem Cell Engraftment," *Stem Cells* 16:166-177 (1998).
Gurdon et al., "Nuclear Reprogramming and Stem Cell Creation," *Proc. Natl. Acad. Sci. U.S.A.* 100 Suppl. 1:11819-11822 (2003).
Gurdon et al., "Reprogramming of Transplanted Nuclei in Amphibia," *Int. Rev. Cytol. Suppl.* 9:161-178 (1979).
Håkelien et al., "Reprogramming Fibroblasts to Express T-Cell Functions Using Cell Extracts," *Nat. Biotechnol.* 20:460-466 (2002).
Hasler, "Current Status and Potential of Embryo Transfer and Reproductive Technology in Dairy Cattle,"*J. Dairy Sci.* 75:2857-2879 (1992).
Hu et al., "Transdifferentiation of Myoblasts by the Adipogenic Transcription Factors PPAR γ and C/EBP α," *Proc. Natl. Acad. Sci. U.S.A.* 92:9856-9860 (1995).
Ishida et al., "Production of a Diverse Repertoire of Human Antibodies in Genetically Engineered Mice," *Microbiol. Immunol.* 42(3):143-150, (1998).
Iwasaki et al., "Production of Live Calves Derived from Embryonic Stem-like Cells Aggregated with Tetraploid Embryos," *Biol. Reprod.* 62:470-475 (2000).
Iwasaki et al., "*In-vitro* Development of Aggregates of Bovine Inner Cell Mass Cells or Bovine Mammary Cells and Putative Tetraploid Embryos Produced by Electrofusion," *Journal of Reproduction and Development* 45:65-71 (1999).
Kasinathan et al., "Production of Calves From G1 Fibroblasts," *Nature Biotech.* 19:1176-1178 (2001).
Kasinathan et al., "Effect of Fibroblast Donor Cell Age and Cell Cycle on Development of Bovine Nuclear Transfer Embryos In Vitro," *Biol. Reprod.* 64:1487-1493 (2001).
Kass et al., "How does DNA Methylation Repress Transcription?," *Trends Genet.* 13:444-449 (1997).
Kato et al., "Germ Cell Nuclei of Male Fetal Mice Can Support Development of Chimeras to Midgestation Following Serial Transplantation," *Development* 121:779-783 (1995).
Kikyo et al., "Reprogramming Nuclei: Insights from Cloning, Nuclear Transfer and Heterokaryons," *J. Cell Sci.* 113:11-20 (2000).
Kikyo et al., "Active Remodeling of Somatic Nuclei in Egg Cytoplasm by the Nucleosomal ATPase ISWI," *Science* 289:2360-2362, 2000.
Kono et al., "Development of Chimaeric Two-Cell Mouse Embryos Produced by Allogenic Exchange of Single Nucleus From Two-and Eight-Cell Embryos," *Gamete. Res.* 24:375-384 (1989).
Kuroiwa et al., "Manipulation of Human Minichromosomes to Carry Greater than Megabase-Sized Chromosome Inserts," *Nature Biotechnol.* 18:1086-1090, (2000).
Kutay et al., "Dominant-Negative Mutants of Importin-β Block Multiple Pathways of Import and Export through the Nuclear Pore Complex," *EMBO J.* 16:1153-1163 (1997).
Landsverk et al., "Reprogrammed Gene Expression In A Somatic Cell-Free Extract," *EMBO Rep.* 3:384-389 (2002).
Li et al., "Activation of Mitogen-Activated Protein Kinases (Erk1 and Erk2) Cascade Results in Phosphorylation of NF-M Tail Domains in Transfected NIH 3T3 Cells," *Eur. J. Biochem.* 262:211-217 (1999).
Lohka et al., "Formation In Vitro of Sperm Pronuclei and Mitotic Chromosomes Induced by Amphibian Ooplasmic Components," *Science* 220:719-721 (1983).
Lohka et al., "Induction of Nuclear Envelope Breakdown, Chromosome Condensation and Spindle Formation in Cell-Free Extracts," *J. Cell Biol.* 101:518-523 (1985).

Macaulay et al., "Assembly of the Nuclear Pore: Biochemically Distinct Steps Revealed with NEM, GTPγS, and BAPTA," *J. Cell Biol.* 132:5-20 (1996).

Maghazachi et al., "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.* 11:765-774 (1997).

Mann, "Inviability of Parthenogenones Is Determined by Pronuclei, Not Egg Cytoplasm," *Nature* 310:66-67 (1984).

Maus et al., "Disassembly of the Drosophila Nuclear Lamina in a Homologous Cell-Free System," *J. Cell Sci.* 108:2027-2035 (1995).

Meinecke-Tillmann, "Über Kerntransplantationen und das Klonen von Säugetieren," *Praktishe Tierarzt* 9:59-67 (1988).

Miake-Lye et al., "Induction of Early Mitotic Events in a Cell-Free System," *Cell* 41:165-175 (1985).

Modlinski et al., "Further Perspectives in Mammalian Embryo Cloning: Establishment, Culture and Possible Use of Embryonic Stem Cells," *Animal Science Papers and Reports—Polish Academy of Sciences* 13:169-184 (1995).

Moreira et al., "Architectural Defects in Pronuclei of Mouse Nuclear Transplant Embryos," *J. Cell Sci.* 116:3713-3720, (2003).

Morrison, "Stem Cell Potential: Can Anything Make Anything," *Curr. Biol.* 11:R7-R9 (2001).

Munsie et al., "Isolation of Pluripotent Embryonic Stem Cells from Reprogrammed Adult Mouse Somatic Cell Nuclei," *Curr. Biol.* 10:989-992 (2000).

Munsie et al., "Novel Method for Demonstrating Nuclear Contribution in Mouse Nuclear Transfer," *Reprod. Fertil. & Dev.* 10:633-637 (1998).

Newmeyer et al., "In Vitro Transport of a Fluorescent Nuclear Protein and Exclusion of Non-Nuclear Proteins," *J. Cell Biol.* 103:2091-2102 (1986).

Newmeyer "Nuclear Import Can be Separated into Distinct Steps In Vitro: Nuclear Pore Binding and Translocation," *Cell* 52:641-653 (1988).

Newmeyer et al., "An N-Ethylmaleimide-Sensitive Cytosolic Factor Necessary for Nuclear Protein Import: Requirement in Signal-Mediated Binding to the Nuclear Pore," *J. Cell Biol.* 110:547-557 (1990).

Newport, "Nuclear Reconstitution In Vitro: Stages of Assembly Around Protein-Free DNA," *Cell* 48:205-217 (1987).

Niemann et al., "Manipulating Early Pig Embryos," *J. Reprod.& Fertil. Suppl.* 48:75-94 (1993).

Notarianni, "Prospects for the Attainment of Transgenesis in Livestock," Abstract No. 4173, *Genetic Engineering Applications,* p. 613.

Overström, "Manipulation of Early Embryonic Development," *Animal Reproduction Science* 28:277-285 (1992).

Paschal et al, "Identification of NTF2, a Cytosolic Factor for Nuclear Import that Interacts with Nuclear Pore Complex Protein p62," *J. Cell Biol.* 129:925-937 (1995).

Perry et al., "Mammalian Oocyte Activation by the Synergistic Action of Discrete Sperm Head Components: Induction of Calcium Transients and Involvement of Proteolysis," *Dev. Biol.* 217:386-393 (2000).

Perry et al., "Mammalian Transgenesis by Intracytoplasmic Sperm Injection," *Science* 284:1180-1183 (1999).

Polejaeva et al., "New Advances in Somatic Cell Nuclear Transfer: Application in Transgenesis," *Theriogenology* 53:117-126 (2000).

Polejaeva et al., "Cloned Pigs Produced by Nuclear Transfer From Adult Somatic Cells," *Nature* 407:86-90 (2000).

Polge, "Potential Impact of Advanced Biotechnology on Genetic Conservation Programmes," in *Genetic Conservation of Domestic Livestock,* edited by Alderson, Wallingford, U.K. pp. 227-235 (1990).

Pollock et al., "Development of Human Lymphocyte-Engrafted SCID Mice as a Model for Immunotoxicity Assessment," *Fund. & Appl. Toxicol.* 22:130-138, (1994).

Prelle et al., "Establishment of Pluripotent Cell Lines from Vertebrate Species—Present Status and Future Prospects," *Cells Tissues Organs* 165:220-236 (1999).

Ramirez et al., "Life-Supporting Human Complement Regulator Decay Accelerating Factor Transgenic Pig Liver Xenograft Maintains the Metabolic Function and Coagulation in the Nonhuman Primate for Up to 8 Days," *Transplantation* 70:989-998 (2000).

Rexroad, "History of Genetic Engineering of Laboratory and Farm Animals," *Genetic Engineering of Animals, An Agricultural Perspective,* pp. 127-138 (1986).

Ribbeck et al., "NTF2 Mediates Nuclear Import of Ran," *EMBO J.* 17:6587-6598 (1998).

Rideout et al., "Generation of Mice From Wild-Type and Targeted ES Cells by Nuclear Cloning," *Nat. Genet.* 24:109-110 (2000).

Rideout et al., "Nuclear Cloning and Epigenetic Reprogramming of the Genome," *Science* 293:1093-1098 (2001).

Risau et al., "Vasculogenesis and Angiogenesis in Embryonic-Stem-Cell-Derived Embryoid Bodies," *Development* 102:471-478 (1988).

Sandrin et al., "Galα(1,3)Gal, the Major Xenoantigen(s) Recognised in Pigs by Human Natural Antibodies," *Immunol. Rev.* 141:169-190 (1994).

Schlenstedt et al., "Reconstitution of Nuclear Protein Transport with Semi-Intact Yeast Cells," *J. Cell Biol.* 123:785-798 (1993).

Schnieke et al., "Human Factor IX Transgenic Sheep Produced by Transfer of Nuclei from Transfected Fetal Fibroblasts," *Science* 278:2130-2133 (1997).

Seidel, "Reproductive Biotechnology and 'Big' Biological Questions," *Theriogenology* 53:187-194 (2000).

Shelton, "Embryo Manipulation in Research and Animal Production," *Aust. J. Biol. Sci.* 41:117-132 (1988).

Shen et al., "Molecular Basis of Transdifferentiation of Pancreas to Liver," *Nat. Cell Biol.* 2:879-887 (2000).

Sotomaru et al., "Induction of Pluripotency by Injection of Mouse Trophectoderm Cell Nuclei into Blastocysts Following Transplantation into Enucleated Oocytes," *Theriogenology* 52:213-220 (1999).

Sotomaru et al., "Nuclear Transplantation of Mouse Inner Cell Mass and Trophectoderm Cells into Endonucleated Two-cell Embryos," *Journal of Reproduction and Development* 44:1-6 (1998).

Steen et al., "Recruitment of Protein Phosphatase 1 to the Nuclear Envelope by A-Kinase Anchoring Protein AKAP149 Is a Prerequisite for Nuclear Lamina Assembly," *J. Cell Biol.* 150:1251-1261 (2000).

Steen et al., "A Kinase-Anchoring Protein (AKAP)95 Recruits Human Chromosome-Associated Protein (hCAP)-D2/Eg7 for Chromosome Condensation in Mitotic Extract," *J. Cell Biol.* 149:531-536 (2000).

Stice et al., "Nuclear Reprogramming in Nuclear Transplant Rabbit Embryos," *Biol. Reprod.* 39:657-664 (1988).

Stice et al., "Bovine Pluripotent Embryonic Cells Contribute to Nuclear Transfer and Chimeric Fetuses," *Theriogenology* 41:301 (1994).

Stice et al., "Pluripotent Bovine Embryonic Cell Lines Direct Embryonic Development Following Nuclear Transfer," *Biol. Reprod.* 54:100-110 (1996).

Sullivan et al., "Cloned Calves From Chromatin Remodeled in Vitro," *Biology of Reproduction* 70:146-153, (2004).

Sun et al., "Immunization with Interleukin-2-Secreting Allogeneic Cells Transfected with DNA from Mouse Melanoma Cells Induces Immune Responses that Prolong the Lives of Mice with Melanoma," *Cancer Gene Therapy* 5:110-118 (1998).

Suprynowicz et al., "A Fractionated Cell-Free System for Analysis of Prophase Nuclear Disassembly," *J. Cell Biol.* 103:2073-2081 (1986).

Tada et al., "Embryonic Germ Cells Induce Epigenetic Reprogramming of Somatic Nucleus in Hybrid Cells," *EMBO J.* 16:6510-6520 (1997).

Tamashiro et al., "Postnatal Growth and Behavioral Development of Mice Cloned from Adult Cumulus Cells," *Biol. Reprod.* 63:328-334 (2000).

Tearle et al., "The α-1,3-Galactosyltransferase Knockout Mouse: Implications for Xenotransplantation," *Transplantation* 61:13-19 (1996).

Wade et al., "Chromatin Remodeling in Nuclear Cloning," *Eur. J. Biochem.* 269:2284-2287 (2002).

Wakayama et al., "Mice Cloned from Embryonic Stem Cells," *Proc. Natl. Acad. U.S.A.* 96:14984-14989 (1999).

Wakayama et al., "Cloning of Male Mice From Adult Tail-Tip Cells," *Nat. Genet.* 22:127-128 (1999).

Wakayama et al., "Nuclear Transfer into Mouse Zygotes," *Nat. Genet.* 24:108-109 (2000).

Wakayama et al., "Differentiation of Embryonic Stem Cell Lines Generated from Adult Somatic Cells by Nuclear Transfer," *Science* 292:740-743 (2001).

Wakayama et al., "The First Polar Body can be Used for the Production of Normal Offspring in Mice," *Biol. Reprod.* 59:100-104 (1998).

Wakayama et al., "Full-Term Development of Mice from Enucleated Oocytes Injected with Cumulus Cell Nuclei," *Nature* 394:369-74 (1998).

Wakayama et al., "Fertilisability and Developmental Ability of Mouse Oocytes with Reduced Amounts of Cytoplasm," *Zygote* 6:341-346 (1998).

Wakayama et al., "Cloning the Laboratory Mouse," *Semin. Cell & Dev. Biol.* 10:253-258, (1999).

Wangh et al., "Efficient Reactivation of *Xenopus* Erythrocyte Nuclei in *Xenopus* Egg Extracts," *J. Cell Sci.* 108:2187-2196 (1995).

Westphal et al., "Transposon-generated 'Knock-out' and 'Knock-in' Gene-Targeting Constructs For Use in Mice," *Current Biology* 7:R530-R533 (1997).

Wilson et al., "A Trypsin-Sensitive Receptor on Membrane Vesicles is Required for Nuclear Envelope Formation In Vitro," *J. Cell Biol.* 107:57-68 (1988).

Yang et al., "Micromanipulation of Mammalian Embryos: Principles, Progress and Future Possibilities," *Theriogenology* 38:315-335 (1992).

Zhou et al., "Developmental Potential of Mouse Embryos Reconstructed from Metaphase Embryonic Stem Cell Nuclei," *Biol. Reprod.* 65:412-419 (2001).

\* cited by examiner

METHODS FOR CLONING NON-HUMAN MAMMALS USING REPROGRAMMED DONOR CHROMATIN OR DONOR CELLS

BACKGROUND OF THE INVENTION

In general, the invention features improved methods for cloning mammals and methods for inserting chromosomes, nuclei, or chromatin masses into recipient cells.

The cloning of mammals allows the production of multiple mammals with an identical DNA content. The donor genetic material used to generate these mammals may be selected or engineered such that the cloned mammals have desirable properties, such as increased resistance to disease. Unfortunately, the efficiency of cloning mammals using donor somatic cells is generally low, resulting in only about 1–2% of nuclear transplant embryos developing to term (Polejaeva et al, Nature 407:86–90, 2000). A significant problem with cloning is the loss of mid to late term pregnancies and the low viability of the offspring. Thus, more efficient methods are needed for cloning mammals. These improved methods may reduce the cost and time required to generate multiple viable offspring.

SUMMARY OF THE INVENTION

The purpose of the present invention is to provide improved methods for cloning mammals. In particular, these methods involve the condensation of a donor nucleus into a chromatin mass to allow the release of nuclear components such as transcription factors that may promote the transcription of genes that are undesirable for the development of the nuclear transplant embryo into a viable offspring. In a related method, a permeabilized cell is incubated with a reprogramming media (e.g., a cell extract) to allow the addition or removal of factors from the cell, and then the plasma membrane of the permeabilized cell is resealed to enclose the desired factors and restore the membrane integrity of the cell. If desired, the steps of any of these methods may be repeated one or more times or different reprogramming methods may be performed sequentially to increase the extent of reprogramming, resulting in greater viability of the cloned fetuses. The invention also provides methods for generating chimeric embryos in which some or all of the placental tissue is from one genetic source and the majority of the fetal tissue is from another genetic source. These chimeric embryos may have fewer placental abnormalities and thus may have an increased survival rate. In addition, a novel method has been developed for the insertion of the chromatin mass or a nucleus into the recipient ooctye that involves the use of fusigenic compounds.

Accordingly, in a first aspect, the invention provides a method of cloning a mammal. This method involves (a) incubating a donor nucleus that has less than four sets of homologous chromosomes (i.e., has fewer than two pairs of complete chromatids) under conditions that allow formation of a chromatin mass without causing DNA replication, (b) inserting the chromatin mass into an enucleated oocyte, thereby forming a nuclear transfer oocyte and (c) transferring the nuclear transfer oocyte or an embryo formed from the nuclear transfer oocyte into the uterus of a host mammal under conditions that allow the nuclear transfer oocyte or embryo to develop into a fetus. In a preferred embodiment, the donor nucleus is incubated with a reprogramming media (e.g., a cell extract) under conditions that allow nuclear or cytoplasmic components such as transcription factors, repressor proteins, or chromatin remodeling proteins to be added to, or removed from, the nucleus or resulting chromatin mass. Preferably, the donor nucleus is contacted with one or more of the following under conditions that allow formation of a chromatin mass: a mitotic extract in the presence or absence of an anti-NuMA antibody, a detergent and/or salt solution, or a protein kinase solution. In other preferred embodiments, the reconstituted oocyte or the resulting embryo expresses lamin A, lamin C, or NuMA protein at a level that is less than 5 fold greater than the corresponding level expressed by a control oocyte or a control embryo with the same number of cells and from the same species.

In a related aspect, the invention provides another method of cloning a mammal. This method involves incubating a permeabilized cell with a reprogramming media (e.g., a cell extract) under conditions that allow the removal of a factor (e.g., a nuclear or cytoplasmic component such as a transcription factor) from a nucleus, chromatin mass, or chromosome of the permeabilized cell or the addition of a factor to the nucleus, chromatin mass, or chromosome, thereby forming a reprogrammed cell. The reprogrammed cell is inserted into an enucleated oocyte, and the resulting oocyte or an embryo formed from the oocyte is transferred into the uterus of a host mammal under conditions that allow the oocyte or embryo to develop into a fetus. In preferred embodiments, the permeabilized cell is contacted with one or more of the following under conditions that allow formation of a chromatin mass: a mitotic extract in the presence or absence of an anti-NuMA antibody, a detergent and/or salt solution, or a protein kinase solution. In yet another preferred embodiment, the permeabilized cell is incubated with an interphase reprogramming media (e.g., an interphase cell extract). In still another preferred embodiment, the nucleus in the permeabilized cell remains membrane-bounded, and the chromosomes in the nucleus do not condense during incubation with this interphase reprogramming media. In certain embodiments, incubating the permeabilized cell in the reprogramming media does not cause DNA replication or only causes DNA replication in less than 50, 40, 30, 20, 10, or 5% of the cells. In other embodiments, incubating the permeabilized cell in the reprogramming media causes DNA replication in at least 60, 70, 80, 90, 95, or 100% of the cells. In various embodiments, the permeabilized cell is formed by incubating an intact cell with a detergent, such as digitonin, or a bacterial toxin, such as Streptolysin O. In yet another preferred embodiment, the reprogrammed cell is incubated under conditions that allow the membrane of the reprogrammed cell to reseal prior to insertion into the oocyte. In other preferred embodiments, the reconstituted oocyte or the resulting embryo expresses lamin A, lamin C, or NuMA protein at a level that is less than 5 fold greater than the corresponding level expressed by a control oocyte or a control embryo with the same number of cells and from the same species.

The invention also provides methods for cloning a mammal that involve the use of cells from two different embryos. For example, cells from a nuclear transfer embryo (e.g., an embryo formed by inserting a cell, nucleus, or chromatin mass into an enucleated oocyte) can be combined with cells from an in vitro fertilized, naturally-occurring, or parthenogenetically activated embryo. Preferably, the majority of the cells and their progeny from the nuclear transfer embryo are incorporated into fetal tissue of the resulting chimeric embryo. At least some of the cells and their progeny from the second embryo are preferably incorporated into placental tissue and promote the viability of the resulting chimeric embryo.

Accordingly, in one such aspect, the invention features a method of cloning a mammal that involves inserting a cell, nucleus, or chromatin mass into an enucleated oocyte, thereby forming a first embryo. One or more cells from the first embryo are contacted with one or more cells from an in vitro fertilized, naturally-occurring, or parthenogenetically activated second embryo, forming a third embryo. The third embryo is transferred into the uterus of a host mammal under conditions that allow the third embryo to develop into a fetus. In one embodiment, at least one of the first embryo and the second embryo is a compaction embryo. In another embodiment, the first embryo and the second embryo are at different cell-stages. The first embryo and the donor cell used to produce the second embryo can be from the same species or from different genuses or species. Preferably, at least 10, 20, 30, 40, 50, 60, 70, 80, 90, 95, or 100% cells in the trophectoderm or placental tissue of the fetus are derived from the second embryo, or at least 30, 40, 50, 60, 70, 80, 90, 95, or 100% cells in the inner cell mass or fetal tissue of the fetus are derived from the first embryo. In other preferred embodiments, the first embryo or the third embryo expresses lamin A, lamin C, or NuMA protein at a level that is less than 5 fold greater than the corresponding level expressed by a control embryo with the same number of cells and from the same species.

In a related aspect, the invention features another method of cloning a mammal. This method involves contacting a donor nucleus with a reprogramming media (e.g., cell extract) under conditions that allow formation of a chromatin mass, and inserting the chromatin mass into an enucleated oocyte, thereby forming a first embryo. One or more cells from the first embryo are contacted with one or more cells from an in vitro fertilized, naturally-occurring, or parthenogenetically activated second embryo, forming a third embryo. The third embryo is transferred into the uterus of a host mammal under conditions that allow the third embryo to develop into a fetus. In a preferred embodiment, the chromatin mass is formed by contacting a donor nucleus that has less than four sets of homologous chromosomes with a reprogramming media under conditions that allow formation of a chromatin mass without causing DNA replication. Preferably, the donor nucleus is contacted with one or more of the following under conditions that allow formation of a chromatin mass: a mitotic extract in the presence or absence of an anti-NuMA antibody, a detergent and/or salt solution, or a protein kinase solution. In various embodiments, both the first embryo and the second embryo are compaction embryos; both the first embryo and the second embryo are precompaction embryos, or one of the embryos is a compaction embryo and the other embryo is a precompaction embryo. The first embryo and the second embryo can be at different cell-stages or at the same cell-stage. The first embryo and the donor nucleus used to produce the second embryo can be from the same species or from different genuses or species. Preferably, at least 10, 20, 30, 40, 50, 60, 70, 80, 90, 95, or 100% cells in the trophectoderm or placental tissue of the fetus are derived from the second embryo, or at least 30, 40, 50, 60, 70, 80, 90, 95, or 100% cells in the inner cell mass or fetal tissue of the fetus are derived from the first embryo. In other preferred embodiments, the first embryo or the third embryo expresses lamin A, lamin C, or NuMA protein at a level that is less than 5 fold greater than the corresponding level expressed by a control embryo with the same number of cells and from the same species.

In another related aspect, the invention features yet another method of cloning a mammal. This method involves incubating a permeabilized cell in a reprogramming media (e.g., cell extract) under conditions that allow the removal of a factor from a nucleus, chromatin mass, or chromosome of the permeabilized cell or the addition of a factor from the reprogramming media to the nucleus, chromatin mass, or chromosome, thereby forming a reprogrammed cell. The reprogrammed cell is inserted into an enucleated oocyte, thereby forming a first embryo. One or more cells from the first embryo are contacted with one or more cells from an in vitro fertilized, naturally-occurring, or parthenogenetically activated second embryo, forming a third embryo. The third embryo is transferred into the uterus of a host mammal under conditions that allow the third embryo to develop into a fetus. In a preferred embodiment, the permeabilized cell is incubated with a reprogramming media (e.g., a cell extract) under conditions that allow nuclear or cytoplasmic components such as transcription factors to be added to, or removed from, the nucleus or resulting chromatin mass. In other preferred embodiments, the permeabilized cell is contacted with one or more of the following under conditions that allow formation of a chromatin mass: a mitotic extract in the presence or absence of an anti-NuMA antibody, a detergent and/or salt solution, or a protein kinase solution. In yet another preferred embodiment, the permeabilized cell is incubated with an interphase reprogramming media (e.g., an interphase cell extract). In still another preferred embodiment, the nucleus in the permeabilized cell remains membrane-bounded, and the chromosomes in the nucleus do not condense during incubation with this interphase reprogramming media. In some embodiments, incubating the permeabilized cell in the reprogramming media does not cause DNA replication or only causes DNA replication in less than 50, 40, 30, 20, 10, or 5% of the cells. In other embodiments, incubating the permeabilized cell in the reprogramming media causes DNA replication in at least 60, 70, 80, 90. 95, or 100% of the cells. In various embodiments, the permeabilized cell is formed by incubating an intact cell with a detergent, such as digitonin, or a bacterial toxin, such as Streptolysin O. In yet another preferred embodiment, the reprogrammed cell is incubated under conditions that allow the membrane of the reprogrammed cell to reseal prior to insertion into the oocyte. In various embodiments, both the first embryo and the second embryo are compaction embryos; both the first embryo and the second embryo are precompaction embryos, or one of the embryos is a compaction embryo and the other embryo is a precompaction embryo. The first embryo and the second embryo can be at different cell-stages or at the same cell-stage. The first embryo and the donor cell used to produce the second embryo can be from the same species or from different genuses or species. Preferably, at least 10, 20, 30, 40, 50, 60, 70, 80, 90, 95, or 100% cells in the trophectoderm or placental tissue of the fetus are derived from the second embryo, or at least 30, 40, 50, 60, 70, 80, 90, 95, or 100% cells in the inner cell mass or fetal tissue of the fetus are derived from the first embryo. In other preferred embodiments, the first embryo or the third embryo expresses lamin A, lamin C, or NuMA protein at a level that is less than 5 fold greater than the corresponding level expressed by a control embryo with the same number of cells and from the same species.

In preferred embodiments of any of the above methods for cloning a mammal using cells from two embryos, part or all of the zona pellucida of the first embryo or second embryo is removed before the cells from each embryo are contacted. In one embodiment, the cells from the first and second embryos are contacted by being placed adjacent to each other in solution or on a solid support. In another embodiment, standard techniques are used to inject cells from the first embryo into the second embryo. The cells can be injected into any region of the second embryo, such as the periphery of the embryo between the zona pellucida and the embryo itself. Exemplary naturally occurring embryos include embryos that are surgically or nonsurgically removed from a pregnant mammal (e.g., a bovine) using standard methods. Exemplary in vitro fertilized embryos include intra-cytoplasmic sperm injection embryos generated using standard methods. It is also contemplated that cells from more than two embryos (e.g., cells from 3, 4, 5, 6, or more embryos) can be combined to form a chimeric embryo for generation of a cloned mammal.

In preferred embodiments of any of the above aspects, the reprogramming media (e.g., a cell extract) is modified by the enrichment or depletion of a factor, such as a DNA methyltransferase, histone deacetylase, histone, protamine, nuclear lamin, transcription factor, activator, or repressor. In other preferred embodiments, the level of expression of NuMA or AKAP95 protein in the oocyte or chimeric embryo is at least 2, 5, 10, or 20-fold greater in the nucleus than in the cytoplasm. In yet other embodiments, at least 30, 40, 50, 60, 70, 80, 90, or 100% of the AKAP95 protein in the oocyte or chimeric embryo is extracted with a solution of 0.1% Triton X-100, 1 mg/ml DNase I, and either 100 mM or 300 mM NaCl. Preferably, the chromatin mass is purified from the reprogramming media (e.g., extract) prior to insertion into the enucleated oocyte. In another preferred embodiment, inserting the chromatin mass into the enucleated oocyte involves contacting the chromatin mass and the oocyte with a fusigenic compound under conditions that allow the chromatin mass to enter the ooctye. In yet another preferred embodiment, the fetus develops into a viable offspring. Preferably, at least 1, 3, 5, 10, 20, 30, 40, 50, 60, 70, 80, or 90% of the nuclear transfer oocytes or embryos develop into viable offspring. In this method, the oocyte containing the chromatin mass or reprogrammed cell may be cultured under conditions that allow cell division and one of the resulting cells may be recloned one or more times. The donor nucleus, donor chromatin mass, or donor cell and the oocyte used in the method may be from the same species, or they may be from different species or genuses. The mammal may be a human or non-human mammal, and the oocyte may be fertilized or unfertilized. Preferably the donor nucleus, chromatin mass, or permeabilized cell is from a $G_1$ or $G_0$ phase cell. In addition, the genomic DNA of the cloned embryo, fetus, or mammal is preferably substantially identical to that of the donor cell. It is also contemplated that the chromatin mass or reprogrammed cell may be inserted into an embryo for the production of a chimeric embryo, fetus, or mammal containing a mixture of cells with DNA substantially identical to that of the chromatin mass or reprogrammed cell and cells with DNA substantially identical to that of the naturally-occurring cells in the embryo. It is also contemplated that a nucleated oocyte may be used in the methods of the invention.

The reprogramming media used in any of the aspects of the invention may or may not contain exogenous nucleotides. In other preferred embodiments, a chromatin mass in a reprogramming media or formed in a permeabilized cell is contacted with a vector having a nucleic acid encoding a gene of interest under conditions that allow random integration or homologous recombination between the nucleic acid in the vector and the corresponding nucleic acid in the genome of the chromatin mass, resulting in the alteration of the genome of the chromatin mass. Due to the lack of an intact plasma membrane and the lack of a nuclear membrane, a chromatin mass in a permeabilized cell or in solution may be easier to genetically modify than a naturally-occurring cell. Examples of cells that may be used to generate reprogramming extracts include embryonic stem cells and adult stem cells from brain, blood, bone marrow, pancreas, liver, skin, or any other organ or tissue. Other exemplary reprogramming cell extracts include oocyte extracts (e.g., bovine or sea urchin oocyte extracts) and male germ cell extracts (e.g., spermatogonia, spermatocyte, spermatid, or sperm extracts from vertebrates, invertebrates, or mammals such as bovine). The donor or permeabilized cell can be non-immortalized or naturally, spontaneously, or genetically immortalized. The donor cell, permeabilized cell, recipient cell, or cytoplast can be from a source of any age, such as an embryo, fetus, youth, or adult mammal. Cells from younger sources may have acquired fewer spontaneous mutations and may have a longer life-span after insertion into an oocyte.

The invention also provides methods of inserting chromosomes, chromatin masses, or nuclei into recipient cells. These methods are useful for transferring donor genetic material into a recipient oocyte for the cloning of a mammal. These methods may also be used to replace the genetic material of one cell with that of another cell.

According to this aspect of the invention, a technique is provided for inserting chromosomes or a chromatin mass into a recipient cell that involves contacting the chromosomes or chromatin mass and the cell with a fusigenic compound under conditions that allow the chromosomes or chromatin mass to enter the recipient cell. In one preferred embodiment, the chromosomes or the chromatin mass are incubated with the fusigenic compound prior to being contacted with the recipient cell. The chromosomes or chromatin mass may be condensed or not condensed, and the chromosomes or chromatin mass and the recipient cell may be from the same species or may be from different species or genuses. In another preferred embodiment, the recipient cell is a fertilized or unfertilized oocyte. Preferably, the recipient cell or the chromosomes are from a human or non-human mammal. In various embodiments, the recipient cell is an adult, fetal, or embryonic cell. In one particular preferred embodiment, all of the chromosomes of a donor cell are inserted into the recipient cell. Preferably, the donor cell is haploid (DNA content of n), diploid (2n), or tetraploid (4n), and the recipient cell is hypodiploid (DNA content of less than 2n), haploid, or enucleated. In another embodiment, the chromosomes are from more than one donor cell, such as two haploid cells. In yet another preferred embodiment, the chromosomes are obtained by contacting a donor nucleus that has less than four sets of homologous chromosomes with a mitotic extract, a detergent and/or salt, or a protein kinase under conditions that allow formation of a chromatin mass without causing DNA replication. Preferred fusigenic compounds include polyethylene glycol (PEG), and lipids such as Lipofectin®, Lipofectamin®, DOTAP®{N-[1 -(2,3-Dioleoyloxy)propyl]-N,N,N-trimethylamonium methylsulfate; $C_{43}H_{83}NO_8S$}, DOSPA®{2,3-dioleyloxy-N-[2(sperminecarboxamido)ethyl]-N,N-dimethyl-1-propanaminium trifuoroacetate}, and DOPE® (dioleoyl phosphatidylethanolamine). Other preferred lipids include neutral and monovalent or multivalent cationic lipids, such as those containing quaternary ammonium groups. Additional preferred lipids have a cholesterol moiety such as that formed from the reaction of the hydroxyl group in cholesterol with a group in the lipid. Still other preferred lipids have a saturated or unsaturated fatty acid that preferably contains between 5 and 10, 10 and 15, 15 and 20, or 20 and 30 carbon atoms, inclusive. These lipids may be synthesized using standard chemical synthesis techniques, obtained from naturally-occurring sources, or purchased from commercially available source (Summers et al., Biophys J. 71(6):3199–206, 1996; Nabekura et al, Pharm Res.13(7):1069–72, 1996; Walter et al., Biophys J. 66(2 Pt 1):366–376, 1994; Yang et al., Biosci Rep.13(3):143–157, 1993; Walter and Siegel, Biochemistry. 6:32(13):3271–3281, 1993). Other preferred fusigenic compounds are phospholipids such as membrane vesicle fractions from sea urchin eggs or any other source (Collas and Poccia, J. of Cell Science 109, 1275:1283, 1996). Preferably, contacting chromosomes with the membrane vesicle fraction does not result in the chromosomes being encapsulated by an intact membrane.

In a related aspect, the invention provides a method of inserting a nucleus into a recipient cell that includes contacting the nucleus and the cell with a fusigenic compound under conditions that allow the nucleus to enter the recipient cell. The fusigenic compound is either a lipid or is not a polymer consisting of identical monomers. Preferably, the nucleus is incubated with the fusigenic compound prior to being contacted with the recipient cell. In various embodiments, the nucleus and the recipient cell are from the same species or are from different species or different genuses. Preferably, the nucleus is haploid, diploid, or tetraploid, and the recipient cell is hypodiploid, haploid, or enucleated. In one preferred embodiment, the recipient cell is a fertilized or unfertilized oocyte. Preferably, the recipient cell or the nucleus is from a human or a non-human mammal. In other embodiments, the recipient cell is an adult, fetal, or embryonic cell. Preferred fusigenic compounds are lipids such as Lipofectin®, Lipofectamin®, DOTAP®, DOSPA®, and DOPE®. Other preferred lipids include neutral lipids and monovalent or multivalent cationic lipids, such as those containing quaternary ammonium groups. Additional preferred lipids have a cholesterol moiety or a saturated or unsaturated fatty acid that preferably contains between 5 and 10, 10 and 15, 15 and 20, or 20 and 30 carbon atoms, inclusive. Other preferred fusigenic compounds are phospholipids such as membrane vesicle fractions from sea urchin eggs or any other source (Collas and Poccia, supra). Preferably, contacting a nucleus with the membrane vesicle fraction does not result in the nucleus being encapsulated by an intact membrane.

In preferred embodiments of various aspects of the invention, the nucleus or chromosomes are from an adult, fetal, or embryonic cell. The nucleus or chromosomes may also be obtained from any of the following preferred donor cells, or they may be inserted into any of the following preferred recipient cells. Examples of preferred cells include differentiated cells such as epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, and muscle cells; and undifferentiated cells such as embryonic cells (e.g., stem cells and embryonic germ cells). In another preferred embodiment, the cell is from the female reproductive system, such as a mammary gland, ovarian cumulus, granulosa, or oviductal cell. Other preferred cells include fetal cells and placental cells. Preferred cells also include those from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus. Preferred non-human mammals include members of the genus Bos. Examples of other preferred mammals include cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, and primates such as monkeys. In yet another preferred embodiment, the nucleus, permeabilized cell, or chromosomes are from a transgenic cell or mammal or contain a mutation not found in the donor cell or not found in a naturally-occurring cell.

Preferred transgenic donor nuclei and donor cells encode proteins that confer improved resistance to disease or parasites in the cloned mammal. Alternatively, the donor nuclei or donor cells may be engineered so that the cloned mammal produces a recombinant product, such as the production of a human protein in the urine, blood, or milk of a bovine. For example, proteins may be expressed in the urine of cattle by inserting a polynucleotide sequence encoding a human protein under the control of an uroplakin promoter. Examples of therapeutic proteins that made be produced in the milk of cloned bovines include human monoclonal antibodies and human clotting factors such as any of factors I to XIII (Voet and Voet, Biochemistry, John Wiley & Sons, New York, 1990). These heterologous proteins may be expressed under the control of a prolactin promoter or any other promoter suitable for expression in the milk of a bovine. For the production of human antibodies in the milk, blood, or other fluids of cloned mammals, standard methods may be used to inactivate or "knockout" the endogenous genes for antibody heavy or light chains so that functional antibodies are no longer encoded by a donor nucleus and to insert genes encoding the heavy and light chains of human IgA, IgD, IgE, IgG, or IgM into the genome of the donor nucleus. Recombinant proteins from these or other tissues or fluids may be purified using standard purification methods (see, for example, Ausubel et al., supra).

It is also contemplated that cells, tissues, or organs from an embryo, fetus, or adult mammal produced using the methods of the invention may be used as a source of material for medical applications, such as the treatment or prevention of disease in humans. For example, cells, tissues, or organs may be developed in vitro from a cloned embryo and then transferred to a mammal (e.g., a human), removed from a cloned mammal and transferred to another mammal of a different species, or removed from a cloned mammal and transferred to another mammal of the same species. For example, neuronal tissue from a cloned mammal may be grafted into an appropriate area in the human nervous system to treat, prevent, or stabilize a neurological disease such as Alzheimer's disease, Parkinson's disease, Huntington's disease, or ALS; or a spinal cord injury. In particular, degenerating or injured neuronal cells may be replaced by the corresponding cells from a cloned mammal. This transplantation method may also be used to treat, prevent, or stabilize autoimmune diseases including, but not limited to, insulin dependent diabetes mellitus, rheumatoid arthritis, pemphigus vulgaris, multiple sclerosis, and myasthenia gravis. In these procedures, the cells that are attacked by the recipient's own immune system may be replaced by transplanted cells. The cloned mammals may also be used as a source of cartilage, bone marrow, or any other tissue or organ.

For the production of a cloned mammal as a source of donor transplant material, the donor nucleus or donor cell used to generate the cloned mammal is preferably modified to encode a heterologous MHC Class I protein having an amino acid sequence substantially identical to the sequence of a MHC Class I protein found in the recipient mammal that will be administered the donor material. Alternatively, the donor nucleus encodes a heterologous MHC Class I protein having an amino acid sequence substantially identical to the sequence of an MHC Class I protein found in another mammal of the same genus or species as the recipient mammal. These donor cells, tissues, or organs from cloned mammals that express heterologous MHC proteins are less likely to elicit an adverse immune response when administered to the recipient mammal. Other preferred donor transplant material is obtained from a cloned mammal that was generated using a donor nucleus or donor cell which was modified to express a heterologous protein that inhibits the complement pathway of the recipient mammal, such as the human complement inhibitor CD59 or the human complement regulator decay accelerating factor (h-DAF) (see, for example, Ramirez et al., Transplantation 15:989–998, 2000; Costa et al., Xenotransplantation 6:6–16, 1999). In yet another preferred embodiment, the donor nucleus or donor cell has a mutation that reduces or eliminates the expression or activity of a galactosyltransferase, such as alpha(l,3)-galactosyltransferase (Tearle et al., Transplantation 61:13–19, 1996; Sandrin, Immunol. Rev. 141:169–190, 1994; Costa et al., Xenotransplantation 6:6–16, 1999). This enzyme modifies cell surface molecules with a carbohydrate that elicits an adverse immune response when cells expressing this galactose alpha(1,3)-galactose epitope are administered to humans. Thus, donor transplant material that has a lower level of expression of this epitope may have a lower incidence of rejection by the recipient mammal.

As used herein, by "chromatin mass" is meant more than one chromosome not enclosed by a membrane. Preferably, the chromatin mass contains all of the chromosomes of a cell. An artificially induced chromatin mass containing condensed chromosomes may be formed by exposure of a nucleus to a mitotic reprogramming media (e.g., a mitotic extract) as described herein. Alternatively, an artificially induced chromatin mass containing decondensed or partially condensed chromosomes may be generated by exposure of a nucleus to one of the following, as described herein: a mitotic extract containing an anti-NuMA antibody, a detergent and/or salt solution, or a protein kinase solution. A chromatin mass may contain discrete chromosomes that are not physically touching each other or may contain two or more chromosomes that are in physical contact.

If desired, the level of chromosome condensation may be determined using standard methods by measuring the intensity of staining with the DNA stain, DAPI. As chromosomes condense, this staining intensity increases. Thus, the staining intensity of the chromosomes may be compared to the staining intensity for decondensed chromosomes in interphase (designated 0% condensed) and maximally condensed chromosomes in mitosis (designated 100% condensed). Based on this comparison, the percent of maximal condensation may be determined. Preferred condensed chromatin masses are at least 50, 60, 70, 80, 90, or 100% condensed. Preferred decondensed or partially condensed chromatin masses are less than 50, 40, 30, 20, or 10% condensed.

By "nucleus" is meant a membrane-bounded organelle containing most or all of the DNA of a cell. The DNA is packaged into chromosomes in a decondensed form. Preferably, the membrane encapsulating the DNA includes one or two lipid bilayers or has nucleoporins.

By "nucleus that has less than four sets of homologous chromosomes" is meant a nucleus that has a DNA content of less than 4 n, where "n" is the number of chromosomes found in the normal haploid chromosome set of a mammal of a particular genus or species. Such a nucleus does not have four copies of each gene or genetic locus. Preferably, the nucleus is diploid and thus has two sets of homologous chromosomes but has less than two complete pairs of chromatids.

By "pronucleus" is meant a haploid nucleus resulting from meiosis or a nuclear transfer pronucleus. The female pronucleus is the nucleus of the oocyte or ovum before fusion with the male pronucleus. The male pronucleus is the sperm nucleus after it has entered the oocyte or ovum at fertilization but before fusion with the female pronucleus. A nuclear transfer pronucleus is a pronucleus (e.g., a diploid pronucleus) that forms after introduction of a donor cell, nucleus, or chromatin mass into an oocyte. The nuclear transfer pronucleus has less than four sets of homologous chromosomes.

By "donor cell" is meant a cell from which a nucleus or chromatin mass is derived, or a permeabilized cell.

By "permeabilization" is meant the formation of pores in the plasma membrane or the partial or complete removal of the plasma membrane.

By "reprogramming media" is meant a solution that allows the removal of a factor from a cell, nucleus, chromatin mass, or chromosome or the addition of a factor from the solution to the cell, nucleus, chromatin mass, or chromosome. Preferably, the addition or removal of a factor increases or decreases the level of expression of an mRNA or protein in the donor cell, chromatin mass, or nucleus or in a cell containing the reprogrammed chromatin mass or nucleus. In another embodiment, incubating a permeabilized cell, chromatin mass, or nucleus in the reprogramming media alters a phenotype of the permeabilized cell or a cell containing the reprogrammed chromatin mass or nucleus relative to the phenotype of the donor cell. In yet another embodiment, incubating a permeabilized cell, chromatin mass, or nucleus in the reprogramming media causes the permeabilized cell or a cell containing the reprogrammed chromatin mass or nucleus to gain or lose an activity relative to the donor cell.

Exemplary reprogramming media include solutions, such as buffers, that do not contain biological molecules such as proteins or nucleic acids. Such solutions are useful for the removal of one or more factors from a nucleus, chromatin mass, or chromosome. Other preferred reprogramming medias are extracts, such as cellular extracts from cell nuclei, cell cytoplasm, or a combination thereof. Exemplary cell extracts include extracts from oocytes (e.g., mammalian, vertebrate, or invertebrate oocytes), male germ cells (mammalian, vertebrate, or invertebrate germ cells such as spermatogonia, spermatocyte, spermatid, or sperm), and stem cells (e.g., adult or embryonic stem cells). Yet other reprogramming media are solutions or extracts to which one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) have been added, or extracts from which one or more factors have been removed. Still other reprogramming media include solutions of detergent (e.g., 0.01% to 0.1%, 0.1% to 0.5%, or 0.5% to 2% ionic or non-ionic detergent such as one or more of the following detergents: SDS, Triton X-100, Triton X-114, CHAPS, Na-deoxycholate, n-octyl glucoside, Nonidet P40, IGEPAL, Tween 20, Tween 40, or Tween 80), salt (e.g., ~0.1, 0.15, 0.25, 0.5, 0.75, 1, 1.5, or 2 M NaCl or KCl), polyamine (e.g., ~1 µM, 10 µM, 100 µM, 1 mM or 10 mM spermine, spermidine, protamine, or poly-L-lysine), a protein kinase (e.g., cyclin-dependent kinase 1, protein kinase C, protein kinase A, MAP kinase, calcium/calmodulin-dependent kinase, CK1 casein kinase, or CK2 casein kinase), and/or a phosphatase inhibitor (e.g., ~10 μM, 100 μM, 1 mM, 10 mM, 50 mM, 100 mM of one or more of the following inhibitors: Na-orthovanadate, Na-pyrophosphate, Na-fluoride, NIPPI, inhibitor 2, PNUTS, SDS22, AKAP149, or ocadaic acid). In some embodiments, the reprogramming medium contains an anti-NuMA antibody. If desired, multiple reprogramming media may be used simultaneously or sequentially to reprogram a donor cell, nucleus, or chromatin mass.

By "interphase reprogramming media" is meant a media (e.g., an interphase cell extract) that induces chromatin decondensation and nuclear envelope formation.

By "mitotic reprogramming media" is meant a media (e.g., a mitotic cell extract) that induces chromatin condensation and nuclear envelope breakdown.

By "reprogrammed cell" is meant a cell that has been exposed to a reprogramming media. Preferably, at least 1, 5, 10, 15, 20, 25, 50, 75, 100, 150, 200, 300, or more mRNA or protein molecules are expressed in the reprogrammed cell that are not expressed in the donor or permeabilized cell. In another preferred embodiment, the number of mRNA or protein molecules that are expressed in the reprogrammed cell, but not expressed in the donor or permeabilized cell, is between 1 and 5, 5 and 10, 10 and 25, 25 and 50, 50 and 75, 75 and 100, 100 and 150, 150 and 200, or 200 and 300, inclusive. Preferably, at least 1, 5, 10, 15, 20, 25, 50, 75, 100, 150, 200, 300, or more MRNA or protein molecules are expressed in the donor or permeabilized cell that are not expressed in the reprogrammed cell. In yet another preferred embodiment, the number of MRNA or protein molecules that are expressed in the donor or permeabilized cell, but not expressed in the reprogrammed cell, is between 1 and 5, 5 and 10, 10 and 25, 25 and 50, 50 and 75, 75 and 100, 100 and 150, 150 and 200, or 200 and 300, inclusive. In still another preferred embodiment, these MRNA or protein molecules are expressed in both the donor cell (i.e., the donor or permeabilized starting cell) and the reprogrammed cell, but the expression levels in these cells differ by at least 2, 5, 10, or 20-fold, as measured using standard assays (see, for example, Ausubel et al., Current Protocols in Molecular Biology, John Wiley & Sons, New York, 2000).

By "addition of a factor" is meant the binding of a factor to chromatin, a chromosome, or a component of the nuclear envelope, such as the nuclear membrane or nuclear matrix. Alternatively, the factor is imported into the nucleus so that it is bounded or encapsulated by the nuclear envelope. Preferably, the amount of factor that is bound to a chromosome or located in the nucleus increases by at least 25, 50, 75, 100, 200, or 500%.

By "removal of a factor" is meant the dissociation of a factor from chromatin, a chromosome, or a component of the nuclear envelope, such as the nuclear membrane or nuclear matrix. Alternatively, the factor is exported out of the nucleus so that it is no longer bounded or encapsulated by the nuclear envelope. Preferably, the amount of factor that is bound to a chromosome or located in the nucleus decreases by at least 25, 50, 75, 100, 200, or 500%.

By "enrichment or depletion of a factor" is meant the addition or removal of a naturally-occurring or recombinant factor by at least 20, 40, 60, 80, or 100% of the amount of the factor originally present in an reprogramming media (e.g., a cell extract). Alternatively, a naturally-occurring or recombinant factor that is not naturally present in the reprogramming media may be added. Preferred factors include proteins such as DNA methyltransferases, histone deacetylases, histones, protamines, nuclear lamins, transcription factors, activators, and repressors; membrane vesicles, and organelles. In one preferred embodiment, the factor is purified prior to being added to the reprogramming media, as described below. Alternatively, one of the purification methods described below may be used to remove an undesired factor from the reprogramming media.

By "purified" is meant separated from other components that naturally accompany it. Typically, a factor is substantially pure when it is at least 50%, by weight, free from proteins, antibodies, and naturally-occurring organic molecules with which it is naturally associated. Preferably, the factor is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques such as those described by Ausubel et al. (Current Protocols in Molecular Biology, John Wiley & Sons, New York, 2000). The factor is preferably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, and panning with a plate-bound antibody.

By "recloned" is meant used in a second round of cloning. In particular, a cell from an embryo, fetus, or adult generated from the methods of the invention may be incubated in a mitotic reprogramming media (e.g., a mitotic cell extract) to form a chromatin mass for insertion into an enucleated oocyte, as described above. Alternatively, the cell may be permeabilized, incubated in a reprogramming media, and inserted into an enucleated oocyte, as described above. Performing two or more rounds of cloning may result in additional reprogramming of the donor chromatin mass or donor cell, thereby increasing the chance of generating a viable offspring after the last round of cloning.

By "viable offspring" is meant a mammal that survives ex utero. Preferably, the mammal is alive for at least one second, one minute, one hour, one day, one week, one month, six months, or one year from the time it exits the maternal host. The mammal does not require the circulatory system of an in utero environment for survival.

By "nuclear transfer oocyte" or "nuclear transplant oocyte" is meant an oocyte in which a donor cell, nucleus, or chromatin mass is inserted or fused. An embryo formed from the oocyte is referred to as a "nuclear transfer" or "nuclear transplant" embryo.

By "embryo" or "embryonic" is meant a developing cell mass that has not implanted into the uterine membrane of a maternal host. Hence, the term "embryo" may refer to a fertilized oocyte; an oocyte containing a donor chromatin mass, nucleus, or reprogrammed cell; a pre-blastocyst stage developing cell mass; or any other developing cell mass that is at a stage of development prior to implantation into the uterine membrane of a maternal host and prior to formation of a genital ridge. An embryo may represent multiple stages of cell development. For example, a one cell embryo can be referred to as a zygote; a solid spherical mass of cells resulting from a cleaved embryo can be referred to as a morula, and an embryo having a blastocoel can be referred to as a blastocyst. An "embryonic cell" is a cell isolated from or contained in an embryo.

By "cells derived from an embryo" is meant cells that result from the cell division of cells in the embryo.

By "chimeric embryo" is meant an embryo formed from cells from two or more embryos. The resulting fetus or offspring can have cells that are derived from only one of the initial embryos or cells derived from more than one of the initial embryos. If desired, the percentage of cells from each embryo are incorporated into the placental tissue and into the fetal tissue can be determined using standard FISH analysis or analysis of a membrane dye added to one embryo.

By "precompaction embryo" is meant an embryo prior to compaction. A precompaction embryo expresses essentially no E-cadherin on the surface of its blastomereres. Preferred precompaction embryos express at least 3, 5, 10, 20, 30, or 40-fold less E-cadherin than a fully compacted embryo of the same species, or express no E-adherin.

By "compaction embryo" is meant an embryo undergoing compaction or following compaction. The blastomeres of a compaction embryo express E-cadherin on their surface. This E-cadherin expression can be measuring using standard methods with an anti- E-cadherin antibody. E-cadherin increases the adherence between blastomeres. Preferred compaction embryos include embryos in which the compaction process is completed. Other preferred compaction embryos express at least 3, 5, 10, 20, 30, or 40-fold more E-cadherin than a precompaction embryo of the same species.

By "fetus" is meant a developing cell mass that has implanted into the uterine membrane of a maternal host. A fetus may have defining features such as a genital ridge which is easily identified by a person of ordinary skill in the art. A "fetal cell" is any cell isolated from or contained in a fetus.

By "parthenogenesis" or "parthenogenetic activation" is meant development of an oocyte or ovum without fusion of its nucleus with a male pronucleus to form a zygote. For example, an oocyte can be induced to divide without fertilization.

By "zona pellucida" is meant a translucent, elastic, non-cellular layer surrounding the oocyte or ovum of many mammals.

By "trophectoderm" is meant the outermost layer of cells surrounding the blastocoel during the blastocyst stage of mammalian embryonic development. Trophectoderm gives rise to most or all of the placental tissue upon further development.

By "inner cell mass" is meant the cells surrounded by the trophectoderm. The inner cell mass cells give rise to most of the fetal tissues upon further development.

By "MRNA or protein specific for one cell type" is meant an mRNA or protein that is expressed in one cell type at a level that is at least 10, 20, 50, 75, or 100 fold greater than the expression level in all other cell types. Preferably, the mRNA or protein is only expressed in one cell type.

By "mutation" is meant an alteration in a naturally-occurring or reference nucleic acid sequence, such as an insertion, deletion, frameshift mutation, silent mutation, nonsense mutation, or missense mutation. Preferably, the amino acid sequence encoded by the nucleic acid sequence has at least one amino acid alteration from a naturally-occurring sequence. Examples of recombinant DNA techniques for altering the genomic sequence of a cell, embryo, fetus, or mammal include inserting a DNA sequence from another organism (e.g., a human) into the genome, deleting one or more DNA sequences, and introducing one or more base mutations (e.g., site-directed or random mutations) into a target DNA sequence. Examples of methods for producing these modifications include retroviral insertion, artificial chromosome techniques, gene insertion, random insertion with tissue specific promoters, homologous recombination, gene targeting, transposable elements, and any other method for introducing foreign DNA. All of these techniques are well known to those skilled in the art of molecular biology (see, for example, Ausubel et al., supra). Chromatin masses, chromosomes, and nuclei from transgenic cells containing modified DNA or donor transgenic cells may be used in the methods of the invention.

By "immortalized" is meant capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2, 5, 10, or 20-fold more cell divisions than the control cell. More preferably, the immortalized cell is capable of undergoing an unlimited number of cell divisions. Examples of immortalized cells include cells that naturally acquire a mutation in vivo or in vitro that alters their normal growth-regulating process. Still other preferred immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al., Immunol. Lett. 65:153–159, 1999; Knight et al., Proc. Nat. Acad. Sci. USA 85:3130–3134, 1988; Shammah et al., J. Immunol. Methods 160–19–25, 1993; Gustafsson and Hinkula, Hum. Antibodies Hybridomas 5:98–104, 1994; Kataoka et al., Differentiation 62:201–211, 1997; Chatelut et al., Scand. J. Immunol. 48:659–666, 1998). Cells can also be genetically modified to express the telomerase gene (Roques et al., Cancer Res. 61:8405–8507, 2001).

By "non-immortalized" is meant not immortalized as described above.

By "fusigenic compound" is meant a compound that increases the probability that a chromatin mass or nucleus is inserted into a recipient cell when located adjacent to the cell. For example, the fusigenic compound may increase the affinity of a chromatin mass or a nucleus for the plasma membrane of a cell. The fusigenic compound may also promote the joining of the nuclear membrane of a nucleus with the plasma membrane of a cell.

By "substantially identical" is meant having a sequence that is at least 60, 70, 80, 90, or 100% identical to that of another sequence. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

The present invention provides a number of advantages related to the cloning of mammals and the transfer of genomic material into recipient cells. For example, the methods may result in a higher percentage of viable offspring, increasing the number of mammals that may be used for agricultural or medical applications. Compared to microinjection, the method described herein for the transfer of chromosomes, chromatin masses, or nuclei into cells, called lipofusion, is a gentler and simpler means of introducing genetic material into cells since it does not require physical disruption of cellular structures or the technical skill needed to pick up a nucleus or chromatin mass using a micropipette and inject it into a cell. The present method may also be safer than fusion methods involving viruses or viral components. Further, lipofusion is believed to elicit minimal, if any, physiological damage to the recipient cell and is therefore beneficial over electrofusion which elicits signaling events inside the fused cells that may impair cell cycle progression or development of the cloned embryo.

Other features and advantages of the invention will be apparent from the following detailed description and from the claims.

BRIEF DESCRIPTION OF THE DRAWINGS

The application file contains drawings executed in color (FIGS. 3, 6A–6C, 8A, and 8B). Copies of this patent or patent application with color drawings will be provided by the Office upon request and payment of the necessary fee.

FIG. 1A is a picture of in vitro-fertilized bovine embryos at the pronuclear and 8-cell stage examined using the same antibodies. Arrows in FIG. 1A to anti-NuMA and anti-AKAP95 labeling in the female pronucleus of pronuclear stage embryos. Insets in FIG. 1A are pictures of DNA labeled with 0.1 μg/ml Hoechst 33342 (bars, 20 μm). FIG. 1B is the immunoblotting analysis of bovine fibroblasts (upper rows) and pronuclear stage embryos (lower rows). Molecular weight markers are shown in kDa on the right of FIG. 1B.

FIG. 2 is a picture of bovine donor fibroblasts (Donor cell), nuclear transplant embryos at the premature chromatin condensation stage (three hours post-fusion), nuclear transplant embryos at the pronuclear stage (19 hours post-fusion), and parthenogenetic pronuclear stage embryos activated as described herein. Disassembly of the donor nucleus and assembly of the new pronuclei were monitored at the premature chromatin condensation stage three hours post injection "hpi" ("PCC") and seven hours post injection ("NT PN"), using anti-lamin B, lamins A/C, NuMA, and AKAP95 antibodies. Female pronuclei formed after parthenogenetic activation of MII oocytes with 10 mM SrCl$_2$ were also analyzed five hours after start of activation treatment ("Parth. PN"). Lamins A/C were assembled in pronuclei of bovine pronuclear stage nuclear transplant embryos. DNA was counterstained with 0.1 μg/ml Hoechst 33342. TRITC refers to labeling with TRITC-conjugated secondary antibodies (bars, 20 μm).

FIG. 4 is a picture of bovine pronuclear nuclear transplant embryos produced by fibroblast fusion and oocyte activation with either 5 μM ionomycin for four minutes followed by 10 μg/ml cycloheximide/2.5 μg/ml cytochalasin D for four hours (b', –), ionomycin/cycloheximide/cytochalasin D as in (b') followed by an additional nine hours of culture with 10 μg/ml cycloheximide (b", CHX) or incubation as in (b') together with 1 μg/ml actinomycin D during the entire activation treatment (b'''). Anti-lamin B (rabbit polyclonal) and anti-lamins A/C (mAb) antibodies were used on the same preparations. Insets are pictures of DNA labeling with 0.1 μg/ml Hoechst 33342 (bars, 20 μm).

FIG. 8A shows the analysis of lamins A/C and B. FIG. 8B shows the analysis of AKAP95 and NuMA. Lamins A/C (green label) only appear in nuclear transplant and nuclear injection pronuclei (bars, 30 μm).

DETAILED DESCRIPTION

Figure 1A:
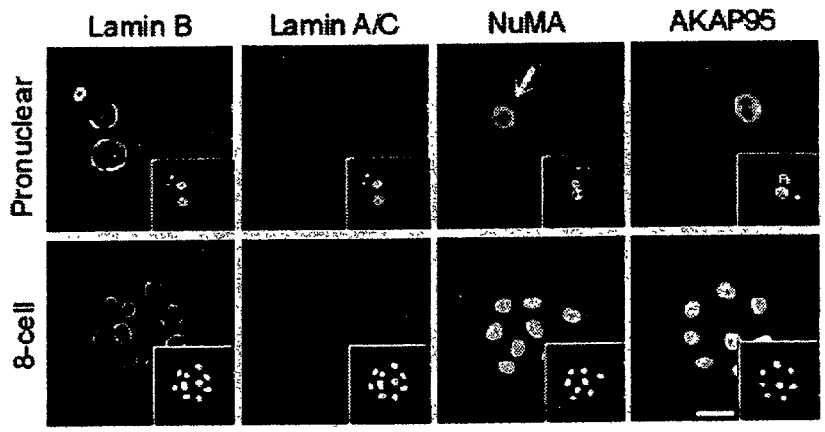
FIGS. 1A and 1B illustrate the immunodetection of nuclear envelope and nuclear matrix proteins in bovine preimplantation embryos.

We have developed a novel method of cloning mammals that involves remodeling of the donor genetic material before it is inserted into the recipient oocyte. Remodeling refers to any morphological change that improves development of the resulting nuclear transplant oocyte over that derived from either transferring whole cells or intact nuclei into a recipient oocyte. Reprogramming is achieved by incubating a donor nucleus in a reprogramming media (e.g., a mitotic extract, detergent and/or salt solution, or protein kinase solution) resulting in nuclear envelope dissolution and possibly chromatin condensation. This nuclear envelope breakdown and chromatin condensation allows the release of transcription regulatory proteins that were attached to the chromosomes and that would otherwise promote the transcription of genes undesirable for oocyte, embryo, or fetus development. Additional regulatory proteins may be removed by purifying the chromatin mass prior to transferring it into a recipient oocyte. Alternatively, specific regulatory proteins that are released from the chromosomes may be immunodepleted or otherwise removed from the reprogrammed media (e.g., a cell extract) to prevent them from re-binding the chromosomes. After nuclear transfer, new proteins from the oocyte cytoplasm may be bound to the chromosomes during decondensation of the chromatin and nuclear envelope formation in the oocyte. These proteins promote the transcription of genes that allow the oocyte to develop into a viable offspring.

This chromatin transfer cloning method produced embryos with protein expression patterns that more closely resembled in vitro fertilized embryos than cloned embryos produced using traditional cloning methods. As illustrated in Examples 1 and 4, chromatin transfer embryos expressed much less lamin A/C protein than traditional nuclear transfer embryos. Lamins A/C are somatic-specific components of the nuclear lamina that are naturally expressed in differentiated cells, but not expressed in embryos. Because of the reported interaction of lamins with transcription factors, chromatin proteins, and DNA, it is likely that the expression of lamins A/C in traditional nuclear transfer embryos promotes the expression of proteins specific for somatic cells that are undesirable for embryo development. Thus, the chromatin transfer embryos of the present invention may express fewer undesirable somatic-specific proteins than traditional nuclear transfer embryos. Additionally, the chromatin transfer embryos had expression patterns for NuMA, a main component of the nuclear matrix that is implicated in transcriptional regulation, that more closely resembled in vitro fertilized embryos than traditional nuclear transplant embryos. This result also indicates that chromatin transfer embryos are more efficiently reprogrammed than traditional nuclear transplant embryos.

Another cloning method was developed that involves reprogramming a permeabilized cell by incubating it in a reprogramming media (e.g., a cell extract) to allow the addition or removal of factors from the cell. The plasma membrane of the permeabilized cell is preferably resealed to enclose the desired factors and restore the membrane integrity of the cell. The reprogrammed cell is then transferred into a recipient ooctye for the production of a cloned mammal. This cloning method has been used to produce fetuses that have survived past day 60. Preliminary results indicate that fetal survival between day 40 and day 60 is higher for fetuses formed using this method (7/10; 70%) than for conventional nuclear transfer fetuses (8/16; 50%).

The invention also provides methods for generating chimeric embryos in which the majority of the placental tissue is from one genetic source and the majority of the fetal tissue is from another genetic source. These chimeric embryos may have fewer placental abnormalities and thus may have an increased survival rate. In one such method, cells from an in vitro fertilized or naturally-occurring embryo are contacted with cells from an embryo produced using traditional nuclear transfer methods or any of the novel cloning methods described herein. For example, cells from an in vitro fertilized embryo can be injected into the periphery of a nuclear transfer embryo (e.g., between the zona pellucida and the embryo itself). This method was used to produce chimeric embryos that had a 67% survival rate at day 40 compared to a 25% survival rate for control nuclear transfer embryos. In an alternative method, cells from a precompaction, in vitro fertilized or naturally-occurring embryo are incubated with cells from a precompaction nuclear transfer embryo under conditions that allow cells from each embryo to reorganize to produce a single chimeric embryo (Wells and Powell, Cloning 2:9–22, 2000). In both methods, the cells from the in vitro fertilized or naturally-occurring embryo are preferentially incorporated into the placenta, and the cells from the nuclear transfer method are preferentially incorporated into the fetal tissue.

The invention also features a novel method, denoted lipofusion, for inserting a nucleus or chromosomes into cells. This method involves incubating the nucleus or chromosomes and the recipient cell with a fusigenic compound that allows the nucleus or chromosomes to be transferred into the cytoplasm of the cell. This method may generally be applied to nuclei and chromosomes from all cell types and to recipient cells of all cell types.

These methods are described further below. It is noted that any of the methods described below can also be performed with reprogramming media other than cell extracts. For example, a reprogramming media can be formed by adding one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) to a solution, such as a buffer. Preferably, one or more of the factors are specific for oocytes or stem cells, such as embryonic stem cells.

EXAMPLE 1

Evidence For Nuclear Reprogramming Deficiencies in Traditional Bovine Nuclear Transplant Embryos Distribution of Nuclear Envelope, Nuclear Matrix, and Chromatin-matrix Interface Components During Bovine Preimplantation Development To determine the distribution of nuclear envelope (B-type and A/C-type lamins), nuclear matrix (NuMA), and chromatin-matrix interface (AKAP95) components in preimplantation embryos, bovine embryos were produced by in vitro fertilization (IVF) and examined by immunofluorescence analysis. Bovine in vitro fertilization was performed as described previously (Collas et al., Mol. Reprod. Devel. 34:212–223, 1993). Briefly, frozen-thawed bovine sperm from a single bull was layered on top of a 45–90% Percoll gradient and centrifuged for 30 minutes at 700×g. The concentration of sperm in the pellet was determined, and the sperm was diluted such that the final concentration at fertilization was $10^6$ spenn/ml. At 22 hours post maturation, oocytes were washed three times in TL HEPES and placed in 480 µl fertilization medium. Twenty µl sperm suspension were added at $10^6$ sperm/ml for 50 oocytes. Embryos were placed in culture in four-well tissue culture plates containing a monolayer of mouse fetal fibroblasts in 0.5 ml of embryo culture medium covered with 0.3 ml of embryo tested mineral oil (Sigma). Between 25 and 50 embryos were placed in each well and incubated at 38.5° C. in a 5% $CO_2$ air atmosphere. Fertilization rates were over 90% as determined by pronuclear development.

For the immunofluorescence analysis of these in vitro fertilized bovine embryos, anti-human lamin B antibodies were obtained from Dr. Jean-Claude Courvalin, CNRS, Paris, France. Anti-lamins A/C monoclonal antibodies were purchased from Santa-Cruz Biotechnology, and anti-NuMA antibodies were obtained from Transduction Laboratories. Anti-rat AKAP95 affinity-purified rabbit polyclonal antibodies were obtained from Upstate Biotechnologies. The in vitro fertilized bovine embryos were settled onto poly-L-lysine-coated glass coverslips, fixed with 3% paraformaldehyde for 15 minutes, and permeabilized with 0.1 % Triton X-100 for 15 minutes (Collas et al, J. Cell Biol. 135: 1715–1725, 1996). The proteins were blocked with 2% BSA in PBS/0.01% Tween 20 (PBST) for 15 minutes. Primary antibodies (anti-AKAP95, anti-lamin B, anti-LBR, anti-NuMA, and anti-lamins A/C) and secondary antibodies were incubated each for 30 minutes and used at a 1:100 dilution in PBST-BSA. DNA was counterstained with 0.1 µg/ml Hoechst 33342 incorporated in the antifade mounting medium. Samples were mounted onto slides and coverslips sealed with nail polish. Immunofluorescence observations were made on an Olympus BX60 epifluorescence microscope and photographs were taken with a JVC CCD camera and AnalySIS software. Images were processed using the Aldus Photostyler software. Relative quantification of fluorescence signals was performed using the AnalySIS quantification program. Data were expressed as mean relative fluorescence intensities.

Immunofluorescence analysis of bovine embryos showed that B-type lamins were detected at the nuclear periphery (FIG. 1A). Lamins A/C, however, were not detected at the pronuclear or 8-cell stage. This failure to detect lamins A/C at these early cell stages is expected for a marker of differentiated cells (Guilli et al., EMBO J. 6:3795–3799, 1987). The nuclear matrix structural protein, NuMA, was detected in all the stages that were examined (FIG. 1A). However, in bovine pronuclear stage embryos, NuMA labeling was restricted to the female pronucleus (FPN), the smallest of both pronuclei (FIG. 1A arrows). AKAP95, which was recently characterized in early mouse embryos (Bomar et al., 2002 manuscript submitted) and detected using affinity-purified anti-rat AKAP95 antibodies, was also restricted to the female pronucleus (FIG. 1A). Nevertheless, intranuclear distribution of AKAP95 was observed in nuclei of all blastomeres in subsequent developmental stages (FIG. 1A).

Figure 1B:
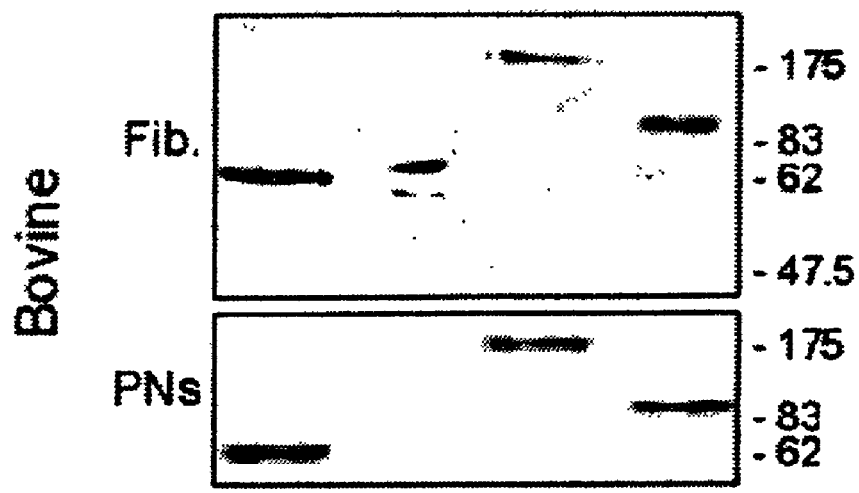

Specificity of immunofluorescence labeling was verified by Western blot analysis of bovine primary fetal fibroblasts and pronuclear stage in vitro fertilized embryos (FIG. 1B). For this analysis, proteins were resolved by 10% SDS-PAGE at 40 mA per gel. Proteins were electrophoretically transferred onto a nitrocellulose membrane in transfer buffer (25mM TrisHC1, pH 8.3, 192 mM glycine, 20% methanol, and 0.1% SDS) at 100 V for one hour. Membranes were washed for 10 minutes with Tris-buffered saline (TB S; i.e., 140 mM NaCl, 2.7 mM KC1, and 25 mM Tris-HC1 at pH 8.0), blocked for one hour with TBST (TBS with 0.05% Tween-20) containing 5% milk, and incubated for 1.5 hours with the following primary antibodies: anti-AKAP95 (1:250 dilution), anti-lamin B (1:1000), anti-LBR (1:500), anti-NuMA (1:500), and anti-lamins A/C (1:500). Blots were washed twice for 10 minutes in TBST and incubated for one hour with horse radish peroxidase (HRP)-conjugated secondary antibodies. Blots were washed twice for 10 minutes in TBS and developed using enhanced chemiluminescence (ECL, Amersham).

All proteins were detected at their expected apparent Mr: 68 kDa (B-type lamins), 70 and 60 kDa (lamins A and C, respectively), ~180 kDa (NuMA), and 95 kDa (AKAP95). Altogether, these results indicate that preimplantation bovine embryos express nuclear structural proteins that can be detected with cross-reacting antibodies. Notably, lamins A/C are not immunologically detected in bovine preimplantation embryos. Because lamins A/C are expressed in somatic cells (FIG. 1B), they potentially constitute molecular markers for nuclear reprogramming in nuclear transplant embryos.

Dynamics of Nuclear Envelope, NuMA, and AKAP95 in Nuclear Transplant Bovine Embryos The dynamics of nuclear envelope and nuclear matrix structures was examined during traditional nuclear transplantation procedure in bovine. These structures were investigated using antibodies to lamins A/C and B, NuMA, and AKAP95, respectively. To determine the dynamics of these markers during nuclear remodeling, bovine nuclear transplant embryos were produced using primary fetal fibroblasts, which were isolated as described previously, as the donor cells (Kasinathan et al., Biol. Reprod. 64:1487–1493, 2001). Briefly, cells were harvested from bovine fetuses by trypsinization using 0.08% trypsin and 0.02% EDTA in PBS (trypsin-EDTA). Cells were seeded in a T75 culture flask (Coming) in α-MEM (Gibco) supplemented with 10% fetal bovine serum (FBS; Hyclone), 0.15 g/ml glutamine (Sigma), 0.003% β-mercaptoethanol (Gibco), and an antibiotic-antimycotic (Gibco). On day three after seeding, cells were harvested with trypsin-EDTA and frozen in α-MEM/DMSO. G1 cells were isolated as described previously (Kasinathan et al., Biol. Reprod. 64:1487–1493, 2001). Briefly, 24 hours before isolation, $5.0 \times 10^5$ cells were plated in a T75 flask containing 10 ml of MEM/FBS. The following day, the plates were washed with PBS, the culture medium was replaced for 1–2 hours, and the plates were shaken for 30–60 seconds on a Vortex at medium speed. The medium was removed, centrifuged at 500×g for five minutes, and the pellet was resuspended in 250 µl of MEM/FBS. Cell doublets attached by a cytoplasmic bridge were selected using a micropipette and used for nuclear transfer.

Bovine nuclear transfer was carried out as described earlier (Kasinathan et al., Biol. Reprod. 64:1487–1493, 2001). In vitro-matured oocytes were enucleated 18–20 hours post-maturation. After transferring G1 donor cells into the perivitelline space, they were fused using a single electrical pulse of 2.4 kV/cm for 20 microseconds (Electrocell Manipulator 200, Genetronics). At 28–30 hours post maturation (i.e., 28–30 hours after oocytes were placed in maturation medium after collection from ovaries and at least two hours after fusion with donor cells) reconstructed oocytes and parthenogenetic controls were activated with calcium ionophore (5 µM) for four minutes (Cal Biochem) followed by 10 µg cycloheximide and 2.5 µg cytochalasin D (Sigma) in ACM medium (100 mM NaCl, 3 mM KCl, 0.27 mM $CaCl_2$, 25 mM $NaHCO_3$, 1 mM sodium lactate, 0.4 mM pyruvate, 1 mM L-glutamine, 3 mg/ml BSA, 1% BME amino acids, and 1% MEM nonessential amino acids, for five hours (Liu et al., Mol. Reprod. Dev. 49:298–307, 1998). After activation, nuclear transplant embryos or oocytes eggs were washed five times and co-cultured with mouse fetal fibroblasts at 38.5° C. in a 5% $CO_2$ atmosphere.

Figure 2:
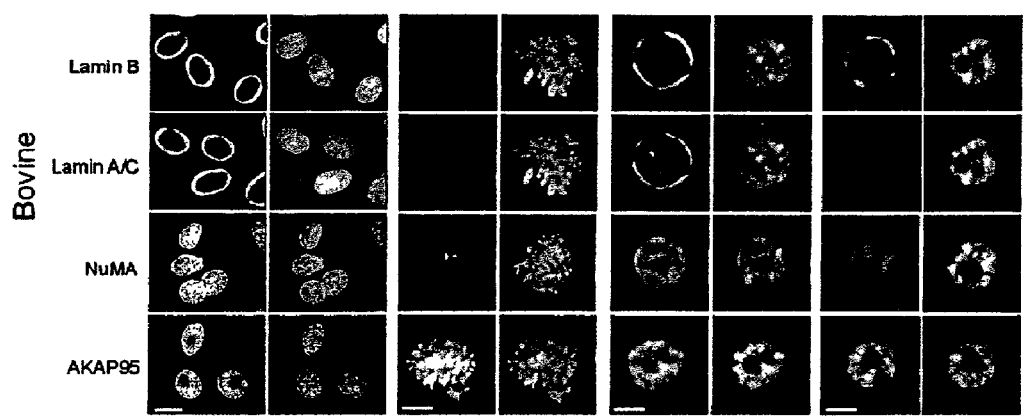
FIG. 2 illustrates the dynamics of the nuclear envelope, NuMA, and AKAP95 during premature chromatin condensation and pronuclear assembly in nuclear transplant embryos.

Reconstituted embryos were activated using standard methods, and three hours post-fusion, embryos at the premature chromatin condensation (PCC) stage were fixed with paraformaldehyde and analyzed by immunofluorescence using antibodies to lamins A/C, lamin B, NuMA, and AKAP95 (FIG. 2, PCC). Furthermore, groups of nuclear transplant embryos that were allowed to progress to the pronuclear (PN) stage (i.e., 15 hour post-fusion bovine embryos) were analyzed similarly (FIG. 2, nuclear transplant-PN). As controls, parthenogenetic oocytes activated as described herein were also examined at the pronuclear stage (FIG. 2, Parth. PN).

As expected, somatic donor cells (bovine fetal fibroblasts, FIG. 2) expressed all markers with a distribution anticipated from the literature. At the premature chromatin condensation stage, distinct condensed chromosome masses were evidenced by DNA staining with Hoechst 33342. Lamins A/C and B were not detected on or near the condensed chromosomes (FIG. 2, PCC), presumably as a result of their dispersal in the egg cytoplasm. Some labeled NuMA was detected; this NuMA was presumably associated with the spindle poles maintaining the condensed chromosomes. AKAP95, in contrast, was associated with the condensed (PCC) chromosomes. This result is reminiscent of AKAP95 labeling in mitotic human cells (Collas et al., J. Cell Biol. 147:1167–1180, 1999; Steen et al., J. Cell Biol. 150:1251–1262, 2000). At the pronuclear stage, all markers were detected. Lamins A/C were present at the pronuclear envelope (FIG. 2, nuclear transplant-PN). This contrasted with their absence from the envelope of control parthenote pronuclei (FIG. 2) and from the envelope of fertilized pronuclei (FIG. 1A). Lamin B was detected in nuclear transplant pronuclei, as in control pronuclei. Likewise, NuMA and AKAP95 decorated the nuclear interior except for the nucleoli. NuMA labeling was consistently brighter in nuclear transplant pronuclei than in control parthenogenetic pronuclei (compare nuclear transplant PN and Parth. PN, FIG. 2). Collectively, these observations indicate that pronuclei of nuclear transplant embryos reassemble the somatic nuclear markers lamins A and C and display strong NuMA staining.

Differential Anchoring of AKAP95 in Pronuclei of Parthenogenetic Embryos and Nuclear Transplant Embryos The A-kinase anchoring protein AKAP95 is a nuclear protein implicated in mitotic chromosome condensation. For use as another molecular marker affecting reprogramming of somatic nuclei after nuclear transplant, the intranuclear anchoring properties of AKAP95 were characterized in bovine nuclear transplant pronuclear stage embryos formed from fetal fibroblasts. Anchoring of AKAP95 in pronuclei from parthenogenetic embryos and nuclei of somatic donor cells was also examined.

Figure 3:
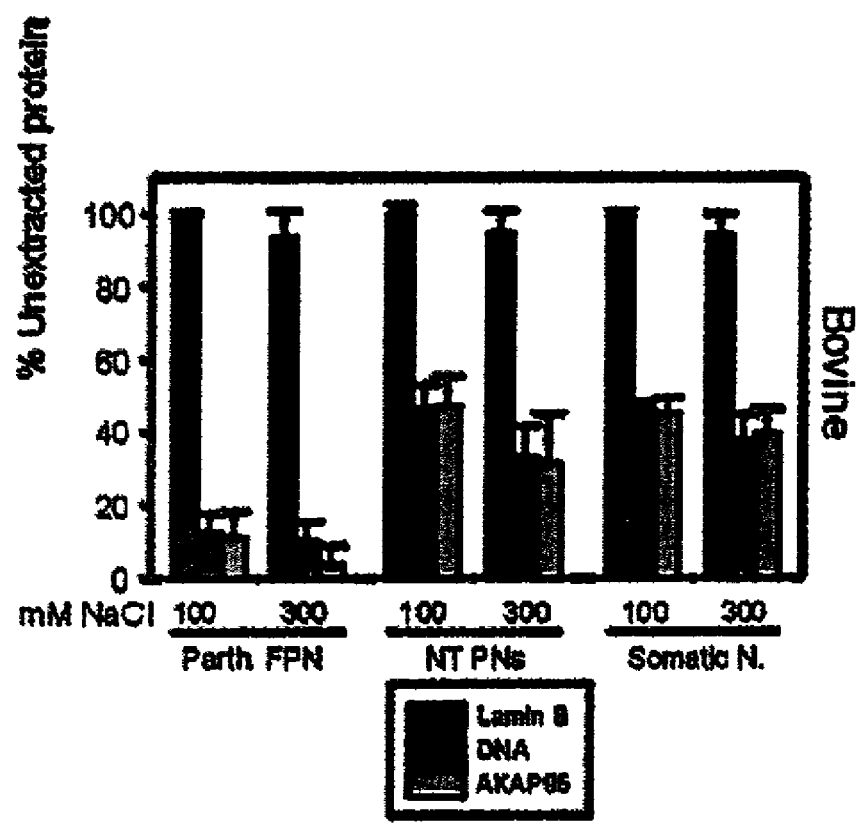
FIG. 3 is a graph demonstrating that AKAP95 is more strongly anchored in pronuclei of nuclear transplant embryos compared to parthenogenetic embryos. This graph shows the relative percent of unextracted lamin B, AKAP95, and DNA labeling in pronuclei of parthenotes, nuclear transplant embryos, and somatic donor nuclei after in situ extraction with 0.1% Triton X-100 and 1 mg/ml DNAse I together with 100 or 300 mM NaCl for 30 minutes at room temperature prior to fixation with 3% paraformaldehyde. Localization of B-type lamins (red) and AKAP95 (green) was examined by double immunofluorescence. Fluorescence labeling intensity in each channel—red, (lamin B), blue (DNA), and green (AKAP95)—was quantified. The reference value (100% unextracted) represents relative amounts of B-type lamins, DNA, and AKAP95 staining in embryos or cells permeabilized with 0.1% Triton X-100 only prior to fixation. Approximately 30 embryos were examined in each group.

Intranuclear anchoring of AKAP95 in pronuclear embryos was examined in situ by extraction of embryos with 0.1% Triton X-100, 1 mg/ml DNAse I, and either 100 or 300 mM NaCl for 30 minutes at room temperature. As noted above, male pronuclei did not harbor any AKAP95. In contrast, a significant amount of AKAP95 and DNA was resistant to DNAse I and 300 mM NaCl in pronuclei of nuclear transplant embryos, and in donor nuclei in bovine (FIG. 3). B-type lamins were not extracted by DNAse I and 300 mM NaCl in parthenote or nuclear transplant pronuclei (FIG. 3), suggesting that alterations in AKAP95 and DNA distributions did not result from gross changes in nuclear architecture. These data indicate that, as in somatic nuclei, AKAP95 is more tightly anchored to intranuclear structures in nuclear transplant pronuclei than in parthenogenetic pronuclei in the bovine. Whether this association imposes constraints on DNA organization or results from altered genome organization in nuclear transplant embryos remains to be determined. As DNAse I-resistant DNA is transcriptionally silent, incomplete remodeling of AKAP95 anchoring after nuclear transplantation likely impairs expression of developmentally important genes.

Transcriptional Misregulation of Lamins A/C in Nuclear Transplant Bovine Embryos A striking observation was that lamins A/C reassemble at the periphery of pronuclei in bovine nuclear transplant embryos, whereas this somatic-specific marker is absent from in vitro fertilized, and parthenogenetic pronuclei. Thus, we investigated whether reassembly of lamins A/C resulted from (i) re-targeting of somatic lamins disassembled at the premature chromatin condensation stage (FIG. 2), (ii) translation and assembly of lamins from a pool of maternal lamin A/C mRNA, or (iii) de novo transcription of the somatic lamin A (LMNA) gene in nuclear transplant pronuclei.

To distinguish between these possibilities, bovine nuclear transplant embryos were produced by either the "traditional" nuclear transplant procedure as described herein, nuclear transplant followed by activation of reconstituted embryos with the protein synthesis inhibitor cycloheximide (CHX), or by nuclear transplant followed by activation in the presence of the RNA polymerase II (PolII) inhibitor actinomycin D (ActD) to inhibit de novo transcription. For culturing bovine nuclear transplant embryos in cycloheximide, oocytes were activated after nuclear transfer as described above except that oocytes were incubated for 14 hours in cycloheximide (CHX). At 14 hours after activation, oocytes were washed five times and placed in ACM culture medium containing 15 µg/ml Hoechst 33342 (Sigma) for one hour. After incubation, pronuclear development was observed by epifluorescence microscopy. Pronuclear embryos were then fixed in 3% paraformaldehyde in PBS, washed, and mounted on slides. For culturing bovine nuclear transplant oocytes in actinomycin D, oocytes were activated after nuclear transfer as described above except 5 µg/ml actinomycin D (ActD) was added to the cycloheximide incubation step. After five hours, eggs were washed five times and placed in ACM culture medium containing 5 µg/ml actinomycin D. At 14 hours after activation, eggs were washed five times and placed in ACM culture medium containing 15 µg/ml Hoechst 33342 (Sigma) for one hour. After incubation, pronuclear development was observed by epifluorescence microscopy. Pronuclear stage embryos were fixed in 3% paraformaldehyde in PBS, washed, and mounted on slides.

Figure 4:
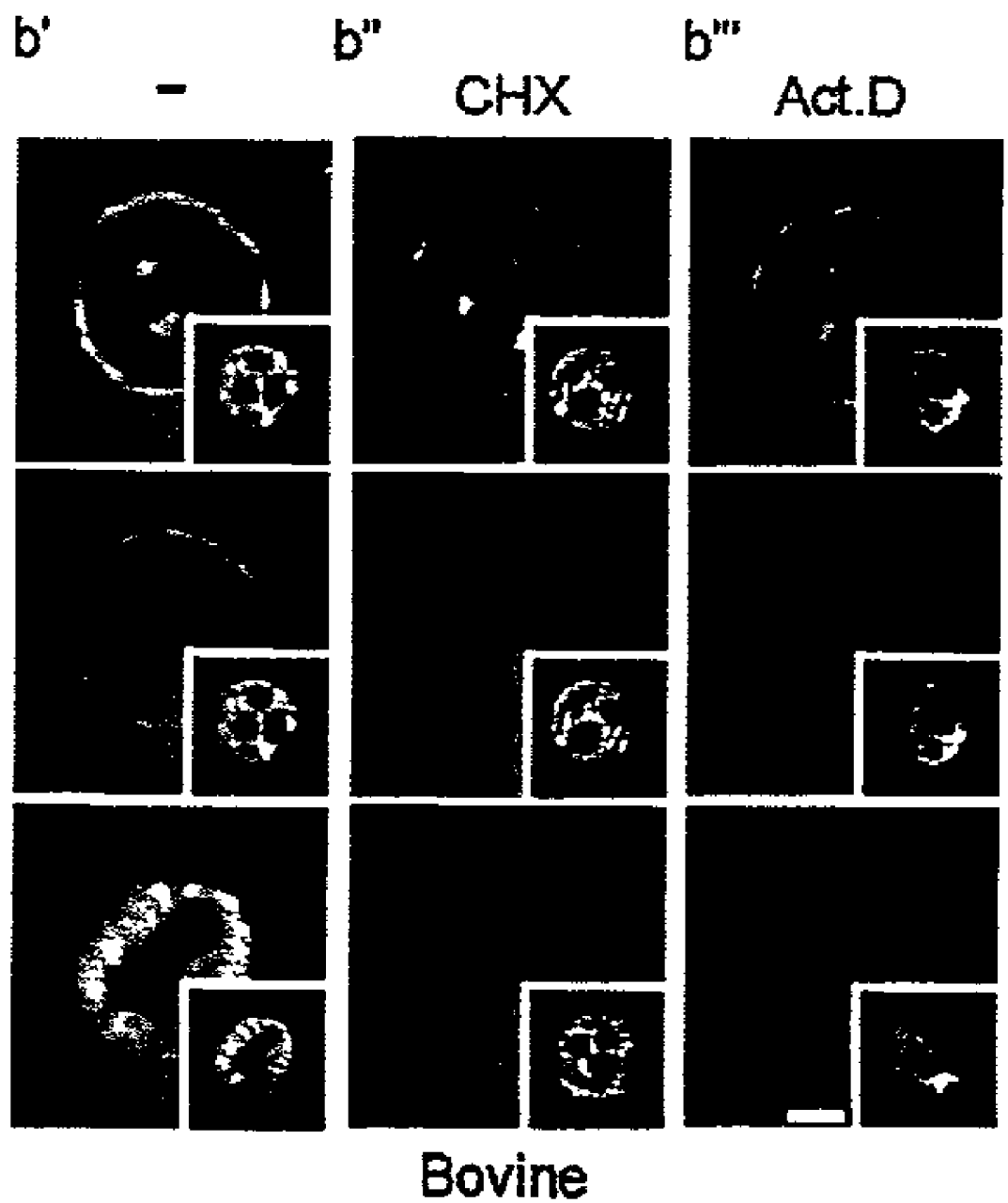
FIG. 4 demonstrates that lamins A/C are transcribed de novo upon pronuclear reconstitution in nuclear transplant embryos.

Lamin B assembly around nuclear transplant pronuclei was not affected by either protein or RNA synthesis inhibition. This result indicates that lamin B was reassembled from either a previously disassembled somatic pool and/or from a large pool of lamin B in the oocyte cytoplasm. Lamins A/C, which were detected in nuclear transplant pronuclei (FIG. 2), were absent from nuclei reformed after activation with cycloheximide. This result indicates that lamins A/C assembly requires de novo protein synthesis and that these lamins are not re-targeted from a disassembled somatic pool brought into the oocyte by donor nucleus injection or cell fusion. Furthermore, lamins A/C are not reassembled when embryos are activated in the presence of actinomycin D. This result indicates that lamins A/C reassembly in nuclear transplant pronuclei results from de novo transcription of the LMNA gene in the reconstituted pronucleus. NuMA, which was detected in nuclear transplant pronuclei, is not reassembled in pronuclei of nuclear transplant embryos activated with cycloheximide, but is faintly detected in pronuclei of actinomycin D-treated nuclear transplant embryos. This finding strongly suggests that NuMA reassembly in nuclear transplant pronuclei requires de novo translation that occurs, at least in part, from a pool of maternal NuMA mRNA. The consistent observation that anti-NuMA labeling is weaker in pronuclei of actinomycin D-treated nuclear transplant embryos compared to control untreated nuclear transplant embryos (compare b' and b'''in FIG. 4) suggests that part of NuMA assembly in nuclear transplant pronuclei results from de novo transcription of the NuMA gene at the pronuclear stage.

Collectively, these results indicate that the LMNA gene is not turned off upon nuclear remodeling after nuclear transplantation. Similarly, the NuMA gene apparently remains active in pronuclear nuclear transplant embryos. It is likely that transient inactivation of these genes takes place during premature chromatin condensation, as anticipated from the highly condensed nature of the chromatin (FIG. 2). These results clearly illustrate incomplete nuclear reprogramming in nuclear transplant embryos produced under the conditions described herein. As discussed earlier for AKAP95, we propose that the persistence of lamins A/C in nuclear transplant pronuclei affects gene expression, such as expression of developmentally important genes. The previously reported interactions of lamins A and C with chromatin proteins and DNA, and the association of these lamins with transcription factors also support this hypothesis.

EXAMPLE 2

Use of Reprogrammed Donor Chromatin Masses to Clone Mammals

To overcome the problem of incomplete reprogramming in traditional nuclear transfer embryos that was demonstrated in Example 1, new methods were developed to more efficiently reprogram donor chromatin prior to nuclear transfer. These methods involve incubating a nucleus from a donor cell in a reprogramming media (e.g., a cell extract) that results in nuclear envelope dissolution and possibly chromatin condensation. This nuclear envelope breakdown and chromatin condensation allows the release of transcription regulatory proteins that were attached to the chromosomes and that would otherwise promote the transcription of genes undesirable for oocyte, embryo, or fetus development. Additionally, regulatory proteins from the reprogramming media may bind the chromatin mass and promote the transcription of genes desirable for development.

Bulk Preparation of Donor Nuclei for Use in Cloning

As many as several million nuclei may be isolated from synchronized or unsynchronized cell populations in culture. The cell populations may be synchronized naturally or chemically. Preferably, at least 40, 60, 80, 90, or 100% of the cells in a population are arrested in $G_0$ or $G_1$ phase. To accomplish this, cells may be incubated, for example, in low serum, such as 5%, 2%, or 0% serum, for 1, 2, 3, or more days to increase the percentage of cells in $G_0$ phase. To synchronize cells in $G_1$, the cells may be grown to confluence as attached cells and then incubated in 0.5–1 µg/ml nocodazole (Sigma Chemicals, St. Louis, Mo.) for 17–20 hours, as described previously (see, for example, Collas et al., J. Cell Biol. 147:1167–1180, 1999 and references therein). The flasks containing the attached cells are shaken vigorously by repeatedly tapping the flasks with one hand, resulting in the detachment of mitotic cells and $G_1$ phase doublets. The $G_1$ phase doublets are pairs of elongated cells at the end of the division process that are still connected by a thin bridge. Detached $G_1$ phase doublets may be isolated from the media based on this characteristic doublet structure. The $G_1$ phase doublets may remain attached or may divide into two separate cells after isolation.

The synchronized or unsynchronized cells are harvested in phosphate buffered saline (PBS) using standard procedures, and several washing steps are performed to transfer the cells from their original media into a hypotonic buffer (10 mM HEPES, pH 7.5, 2 mM $MgCl_2$, 25 mM KCl, 1 mM DTT, 10 µM aprotinin, 10 µM leupeptin, 10 µM pepstatin A, 10 µM soybean trypsin inhibitor, and 100 µM PMSF). For example, the cells may be washed with 50 ml of PBS and pelleted by centrifugation at 500×g for 10 minutes at 4° C. The PBS supernatant is decanted, and the pelleted cells are resuspended in 50 ml of PBS and centrifuged, as described above. After this centrifugation, the pelleted cells are resuspended in 20–50 volumes of ice-cold hypotonic buffer and centrifuged at 500×g for 10 min at 4° C. The supernatant is again discarded and approximately 20 volumes of hypotonic buffer are added to the cell pellet. The cells are carefully resuspended in this buffer and incubated on ice for at least one hour, resulting in the gradual swelling of the cells.

To allow isolation of the nuclei from the cells, the cells are lysed using standard procedures. For example, 2–5 ml of the cell suspension may be transferred to a glass homogenizer and Dounce homogenized using an initial 10–20 strokes of a tight-fitting pestle. Alternatively, the cell suspension is homogenized using a motorized mixer (e.g., Ultraturrax). If desired, cell lysis may be monitored using phase contrast microscopy at 40-fold magnification. During this homogenization, the nuclei should remain intact and most or preferably all of the originally attached cytoplasmic components such as vesicles, organelles, and proteins should be released from the nuclei. If necessary, 1–20 µg/ml of the cytoskeletal inhibitors, cytochalasin B or cytochalasin D, may be added to the aforementioned hypotonic buffer to facilitate this process. Homogenization is continued as long as necessary to lyse the cells and release cytoplasmic components from the nuclei. For some cell types, as many as 100, 150, or more strokes may be required. The lysate is then transferred into a 15 ml conical tube on ice, and the cell lysis procedure is repeated with the remainder of the suspension of swollen cells. Sucrose from a 2 M stock solution made in hypotonic buffer is added to the cell lysate (e.g., ⅛ volume of 2 M stock solution is added to the lysate), resulting in a final concentration of 250 mM sucrose. This solution is mixed by inversion, and the nuclei are pelleted by centrifugation at 400×g in a swing out rotor for 10 to 40 minutes at 4° C. The supernatant is then discarded, and the pelleted nuclei are resuspended in 10–20 volumes of nuclear buffer (10 mM HEPES, pH 7.5, 2 mM $MgCl_2$, 250 mM sucrose, 25 mM KCl, 1 mM DTT, 10 µM aprotinin, 10 µM leupeptin, 10 µM pepstatin A, 10 µM soybean trypsin inhibitor, and 100 µM PMSF). The nuclei are sedimented and resuspended in 1–2 volumes of nuclear buffer, as described above. The freshly isolated nuclei may either be used immediately for in vitro reprogramming and nuclear transfer as described below or stored for later use. For storage, the nuclei are diluted in nuclear buffer to a concentration of approximately $10^6$/ml. Glycerol (2.4 volumes of 100% glycerol) is added and mixed well by gentle pipetting. The suspension is aliquoted into 100–500 µl volumes in 1.5-ml tubes on ice, immediately frozen in a methanol-dry ice bath, and stored at −80° C. Prior to use, aliquots of the nuclei are thawed on ice or at room temperature. One volume of ice cold nuclear buffer is added, and the solution is centrifuged at 1,000×g for 15 minutes in a swing out rotor. The pelleted nuclei are resuspended in 100–500 µl nuclear buffer and centrifuged as described above. The pelleted nuclei are then resuspended in a minimal volume of nuclear buffer and stored on ice until use.

Preparation of Mitotic Extract or Media for Use in Reprogramming Donor Genetic Material For the preparation of a mitotic extract, a somatic cell line (e.g., fibroblasts) is synchronized in mitosis by incubation in 0.5–1 µg/ml nocodazole for 17–20 hours (e.g., Collas et al., J. Cell Biol. 147:1167–1180, 1999 and references therein) and the mitotic cells are detached by vigorous shaking, as described above. The detached $G_1$ phase doublets may be discarded, or they may be allowed to remain with the mitotic cells which constitute the majority off the detached cells (typically at least 80%). The harvested detached cells are centrifuged at 500×g for 10 minutes in a 10 ml conical tube at 4° C. Several cell pellets are pooled, resuspended in a total volume of 50 ml of cold PBS, and centrifuged at 500×g for 10 minutes at 4° C. This PBS washing step is repeated. The cell pellet is resuspended in approximately 20 volumes of ice-cold cell lysis buffer (20 mM HEPES, pH 8.2, 5 mM $MgCl_2$, 10 mM EDTA, 1 mM DTT, 10 µM aprotinin, 10 µM leupeptin, 10 µM pepstatin A, 10 µM soybean trypsin inhibitor, 100 µM PMSF, and optionally 20 µg/ml cytochalasin B), and the cells are sedimented by centrifugation at 800×g for 10 minutes at 4° C. The supernatant is discarded, and the cell pellet is carefully resuspended in no more than one volume of cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract.

The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 µl pipette tip, and the supernatant from several tubes is pooled and placed on ice. This supernatant is the "mitotic cytoplasmic" or "MS 15" extract. This cell extract may be aliquoted into 50 µl or 10 µl volumes of extract per tube on ice, depending on whether the regular or micromethod for generation of chromatin masses will be used. The extracts are immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the MS15 extract. At the end of centrifugation, the oil is discarded. The supernatant is carefully collected, pooled if necessary, and placed in a cold 1.5 ml tube on ice. This supernatant is referred to as "MS200" or "mitotic cytosolic" extract. The extract is aliquoted and frozen as described for the MS15 extract.

If desired, the extract can be enriched with additional nuclear factors. For example, nuclei can be purified from cells of the cell type from which the reprogramming extract is derived or from cells of any other cell type and lysed by sonication as described above. The nuclear factors are extracted by a 10–60 minute incubation in nuclear buffer containing NaCl or KCl at a concentration of 0.15–800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the nuclei for reprogramming.

Mitotic extracts can also be prepared from germ cells, such as oocytes or male germ cells. For example, metaphase II oocytes that are naturally arrested at this stage can be harvested, washed, and lysed as described above for the generation of an oocyte extract. To prepare a male germ cell extract, germ cells are isolated from testes obtained from the abattoir by mincing the organ and by differential centrifugation of the harvested cells on a sucrose or percoll gradient. Germ cells are separated from somatic (Leydig and Sertoli) cells, washed by suspension, and sedimentation in PBS. The cells are then washed once in ice-sold cell lysis buffer as described above and lysed by sonication. The lysate is cleared by centrifugation at 15,000×g for 15 minutes at 4° C., and the supernatant (i.e., the germ cell extract) is aliquoted and snap-frozen in liquid nitrogen.

As an alternative to a cell extract, a reprogramming media can also be formed by adding one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) to a solution, such as a buffer. Preferably, one or more of the factors are specific for oocytes or stem cells.

Formation of Condensed Chromatin Masses by Exposure of Nuclei to a Mitotic Extract or Media An aliquot of MS 15 or MS200 extract or the mitotic media is thawed on ice. An ATP-generating system (0.6 µl) is added to 20 µl of extract or media and mixed by vortexing. For the preparation of the ATP-generating system, equal proportions of 100 mM ATP stock, 1 M creatine phosphate, and 2.5 mg/ml creatine kinase stock solutions (100×) made in $H_2O$ are mixed and stored on ice until use. After addition of the ATP generating system to the extract, the final concentrations are 1 mM ATP, 10 mM creatine phosphate, and 25 µg/ml creatine kinase.

The nuclei suspension is added to the extract or media at a concentration of 1 µl nuclei per 10 µl of extract or media, mixed well by pipetting, and incubated in a 30, 33, 35, 37, or 39° C. water bath. The tube containing the mixture is tapped gently at regular intervals to prevent chromosomes from clumping at the bottom of the tube. Nuclear envelope breakdown and chromosome condensation is monitored at regular intervals, such as every 15 minutes, under a microscope. When the nuclear envelope has broken down and chromosomes have started to condense, the procedure for recovery of chromatin masses from the extract or media is started.

Formation of Decondensed Chromatin Masses by Exposure of Nuclei to a Mitotic Extract or Media and Anti-NuMA Antibodies Alternatively, chromatin masses that are not condensed or only partially condensed may be formed by performing the above procedure after pre-loading the isolated nuclei with an antibody to the nuclear matrix protein NuMA (Steen et al., J. Cell Biol. 149, 531–536, 2000). This procedure allows the removal of nuclear components from chromatin by the dissolution of the nuclear membrane surrounding the donor nuclei; however, the condensation step is inhibited by addition of the anti-NuMA antibody. Preventing chromosome condensation may reduce the risk of chromosome breakage or loss while the chromosomes are incubated in the mitotic extract.

For this procedure, purified cell nuclei (2,000 nuclei/µl) are permeabilized in 500 µl nuclear buffer containing 0.75 µg/ml lysolecithin for 15 minutes at room temperature. Excess lysolecithin is quenched by adding 1 ml of 3% BSA made in nuclear buffer and incubating for 5 minutes on ice. The nuclei are then sedimented and washed once in nuclear buffer. The nuclei are resuspended at 2,000 nuclei/µl in 100 µl nuclear buffer containing an anti-NuMA antibody (1:40 dilution; Transduction Laboratories). After a one hour incubation on ice with gentle agitation, the nuclei are sedimented at 500×g through 1 M sucrose for 20 minutes. The nuclei are then resuspended in nuclear buffer and added to a mitotic extract or media containing an ATP regenerating system, as described in the previous section. Optionally, the anti-NuMA antibody may be added to the extract or media to further prevent chromosome condensation.

Formation of Decondensed Chromatin Masses by Exposure of Nuclei to a Detergent and/or Salt Solution or to a Protein Kinase Solution Chromatin masses that are not condensed or only partially condensed may also be formed by exposure to a detergent or protein kinase. Detergent may be used to solubilize nuclear components that are either unbound or loosely bound to the chromosomes in the nucleus, resulting in the removal of the nuclear envelope. For this procedure, purified cell nuclei (2,000–10,000 nuclei/μl) are incubated in nuclear buffer supplemented with a detergent, such as 0.1% to 0.5% Triton X-100 or NP-40. To facilitate removal of the nuclear envelope, additional salt, such as NaCl, may be added to the buffer at a concentration of approximately 0.1, 0.15, 0.25, 0.5, 0.75, or 1 M. After a 30–60 minute incubation on ice with gentle shaking, the nuclei are sedimented by centrifugation at 1,000×g in a swing-out rotor for 10–30 minutes, depending on the total volume. The pelleted nuclei are resuspended in 0.5 to 1 ml nuclear buffer and sedimented as described above. This washing procedure is repeated twice to ensure complete removal of the detergent and extra salt.

Alternatively, the nuclear envelope may be removed using recombinant or naturally-occurring protein kinases, alone or in combination. Preferably, the protein kinases are purified using standard procedures or obtained in purified form from commercial sources. These kinases may phosphorylate components of the nuclear membrane, nuclear matrix, or chromatin, resulting in removal of the nuclear envelope (see, for example, Collas and Courvalin, Trends Cell Biol. 10: 5–8, 2000). Preferred kinases include cyclin-dependent kinase 1 (CDK1), protein kinase C (PKC), protein kinase A (PKA), MAP kinase, calcium/calmodulin-dependent kinase (CamKII), and CK1 casein kinase, or CK2 casein kinase. For this method, approximately 20,000 purified nuclei are incubated in 20 μl of phosphorylation buffer at room temperature in a 1.5 ml centrifuge tube. A preferred phosphorylation buffer for CDK1 (Upstate Biotechnology) contains 200 mM NaCl, 50 mM Tris-HCl (pH 7.2–7.6), 10 mM MgSO$_4$, 80 mM β-glycerophosphate, 5 mM EGTA, 100 μM ATP, and 1 mM DTT. For PKC, a preferred buffer contains 200 mM NaCl, 50 mM Tris-HCl (pH 7.2–7.6), 10 mM MgSO$_4$, 100 μM CaCl$_2$, 40 μg/ml phosphatidylserine, 20 μM diacylglycerol, 100 μM ATP, and 1 mM DTT. If both PKC and CDK1 are used simultaneously, the CDK1 phosphorylation buffer supplemented with 40 μg/ml phosphatidylserine and 20 μM diacylglycerol is used. A preferred phosphorylation buffer for PKA includes 200 mM NaCl, 10 mM MgSO4, 10 mM Tris, pH 7.0, ImM EDTA, and 100 μM ATP. For MAP kinase, the PKA phosphorylation buffer supplemented with 10 mM CaCl$_2$, and 1 mM DTT maybe used. For CamKII, either PKA buffer supplemented with 1 mM DTT or a Cam Kinase assay kit from Upstate Biotechnology (Venema et al J. Biol. Chem 272: 28187–90, 1997) is used.

The phosphorylation reaction is initiated by adding a protein kinase to a final amount of 25–100 ng. The reaction is incubated at room temperature for up to one hour. Nuclear envelope breakdown may be monitored by microscopy during this incubation, such as at 15 minute intervals. After nuclear envelope breakdown, nuclei are washed three times, as described above for the removal of the detergent solution.

Recovery of Chromatin Masses from the Media, Extract, Detergent and/or Salt Solution, or Protein Kinase Solution The extract or solution containing the condensed, partially condensed, or not condensed chromatin masses is placed under an equal volume of 1 M sucrose solution made in nuclear buffer. The chromatin masses are sedimented by centrifugation at 1,000×g for 10–30 minutes depending on the sample volume in a swing out rotor at 4° C. The supernatant is discarded, and the pelleted chromatin masses are carefully resuspended by pipetting in 0.1–1.0 ml nuclear buffer or lipofusion buffer (150 mM NaCl, 10 μM aprotinin, 10 μM leupeptin, 10 μM pepstatin A, 10 μM soybean trypsin inhibitor, and 100 μM PMSF in either 20 mM HEPES around pH 7.0 or pH 7.5 or 20 mM MES around pH 6.2) and centrifuged at 1,000×g for 10–30 minutes. The supernatant is discarded, and the pelleted chromatin masses are resuspended in nuclear buffer or lipofusion buffer and stored on ice until use. Each chromatin mass is transferred to a 20 μl drop of HEPES-buffered medium under oil in a micromanipulation dish. One chromatin mass is inserted into each enucleated oocyte, as described below.

Micromethod for Preparation of Chromatin Masses

A 10–20 μl drop of MS 15 or MS200 extract or mitotic media containing an ATP generating system, a detergent and/or salt solution, or a protein kinase solution as described above is placed in a petri dish. A 50-μl drop of isolated G$_1$ phase cell doublets or Go phase cells in culture medium, a separate 50 μl "lysis" drop of HEPES- or bicarbonate-buffered medium containing 0.1% Triton X- 100 or NP-40 for use in facilitating cell lysis, and a 50-μl drop of oocyte injection medium is then added. Each of these drops is covered with CO$_2$ equilibrated mineral oil. A 50 μl "wash drop" of culture medium is also added to the petri dish for use in washing the lysed cells or nuclei.

Cells are transferred to the lysis drop using a micropipette. The cell membranes are lysed in the pipette by gentle repeated aspirations. When the cell is lysed, the lysate is gently expelled into the wash drop, and the nucleus is immediately reaspirated to remove detergent. Optionally, the nuclei may be permeabilized and incubated with anti-NuMA antibodies prior to being added to the mitotic extract or media. The nucleus is then expelled into the drop of MS15, MS200, or media, detergent and/or salt solution, or protein kinase solution. Nuclear breakdown and chromosome condensation is monitored as described above. Once the nuclear envelope has broken down and, if a mitotic extract without anti-NuMA antibodies was used, the chromosomes have started to condense, a single intact chromatin mass is isolated with a micropipette and transferred to an enucleated recipient oocyte, as described below.

Enucleation of Oocytes

Preferably, the recipient oocyte is a metaphase II stage oocyte. At this stage, the oocyte may be activated or is already sufficiently activated to treat the introduced chromatin mass as it does a fertilizing sperm. For enucleatation of the oocyte, part or preferably all of the DNA in the oocyte is removed or inactivated. This destruction or removal of the DNA in the recipient oocyte prevents the genetic material of the oocyte from contributing to the growth and development of the cloned mammal. One method for destroying the pronucleus of the oocyte is exposure to ultraviolet light (Gurdon, in *Methods in Cell Biology, Xenopus Laevis:— Practical Uses in cell and Molecular Biology*, Kay and Peng, eds., Academic Press, California, volume 36:pages 299–309, 1991). Alternatively, the oocyte pronucleus may be surgically removed by any standard technique (see, for example, McGrath and Solter, Science 220:1300–1319, 1983). In one possible method, a needle is placed into the oocyte, and the nucleus is aspirated into the inner space of the needle. The needle may then be removed from the oocyte without rupturing the plasma membrane (U.S. Pat. Nos. 4,994,384 and 5,057,420).

Lipofusion for Insertion of Chromatin Masses into Oocytes

Chromatin may be introduced into recipient oocytes by lipofusion as described below or by standard microinjection or electrofusion techniques (see, for example, U.S. Pat. Nos. 4,994,384 and 5,945,577). The following lipofusion method may also be used in other applications to insert chromosomes into other recipient cells.

Chromatin masses are isolated from the mitotic extract, detergent and/or salt solution, or protein kinase solution by centrifugation, and then washed with lipofusion buffer, as described above. The chromatin masses may be in stored in ice-cold lipofusion buffer until use. Alternatively, the chromatin masses are aliquoted, frozen in liquid nitrogen or in a methanol-dry ice bath, and stored frozen at −80° C. The lipofusion solution is prepared by mixing one or more fusigenic reagents with the lipo fusion buffer in respective proportions ranging from 5:1 to 1:10 approximately. The fusigenic reagents consist of, but are not limited to, polyethylene glycol (PEG) and lipophilic compounds such as Lipofectin®, Lipofectamin®, DOTAP®, DOSPA®, DOPE®, and membrane vesicle fractions. For example, a cationic lipid, such as DOTAP®, may be used at a concentration of approximately 0.1 to 30 µg/ml in lipofusion buffer. Alternatively, a liposome formulation consisting of a mixture of a cationic lipid and a neutral lipid, such as DOPE®, may be used.

The chromatin masses, either freshly prepared or frozen and thawed, are mixed with the lipofusion solution to allow coating of the chromatin masses with the compound. Incubation takes place at a temperature of 20–30° C. for a period of approximately 10–30 minutes. Microdrops containing the chromatin masses in the lipofusion solution are placed under $CO_2$ equilibrated mineral oil. A drop containing the enucleated recipient oocytes is also prepared. The chromatin masses coated with the lipofusion reagent are picked up in a micropipette and inserted in the perivitellin space, between the oocyte cytoplasm and the zona pellucida. The chromatin mass is placed next to the oocyte membrane to ensure contact with the oocyte. The chromatin mass-oocyte complexes are maintained at a temperature of 20–30° C., and fusion is monitored under the microscope. Once fusion has occurred, reconstituted oocytes are activated as described below.

Activation Culturing, and Transplantation of Reconstituted Oocytes

To prevent polar body extrusion and chromosome loss, the oocyte may be activated in the presence of cytochalasin B, or cytochalasin B may be added immediately after activation (Wakayama et al., PNAS 96:14984–14989, 1999; Wakayama et al., Nature Genetics 24:108–109, 2000). Either electrical or non-electrical means may be used for activating reconstituted oocytes. Electrical techniques for activating cells are well known in the art (see, for example, U.S. Pat. Nos. 4,994,384 and 5,057,420). Non-electrical means for activating cells may include any method known in the art that increases the probability of cell division. Examples of non-electrical means for activating an oocyte include incubating the oocyte in the presence of ethanol; inositol trisphosphate; $Ca^{++}$ ionophore and a protein kinase inhibitors; a protein synthesis inhibitor; phorbol esters; thapsigargin, or any component of sperm. Other non-electrical methods for activation include subjecting the oocyte to cold shock or mechanical stress. Alternatively, one to three hours after nuclear transfer, oocytes may be incubated for approximately six hours in medium containing $Sr^{2+}$ to activate them and cytochalasin B to prevent cytokinesis and polar body extrusion (Wakayama et al., PNAS 96:14984–14989, 1999; Wakayama et al., Nature Genetics 24:108–109, 2000). Depending on the type of mammal cloned, the preferred length of activation may vary. For example, in domestic animals such as cattle, the oocyte activation period generally ranges from about 16–52 hours or preferably about 28–42 hours.

After activation, the oocyte is placed in culture medium for an appropriate amount of time to allow development of the resulting embryo. At the two cell stage or a later stage, the embryo is transferred into a foster recipient female for development to term. For bovine species, the embryos are typically cultured to the blastocyst stage (e.g., for approximately 6–8 days) before being transferred to maternal hosts. For other cloned animals, an appropriate length for in vitro culturing is known by one skilled in the art or may be determined by routine experimentation.

Methods for implanting embryos into the uterus of a mammal are also well known in the art. Preferably, the developmental stage of the embryo is correlated with the estrus cycle of the host mammal. Once the embryo is placed in the uterus of the mammal, the embryo may develop to term. Alternatively, the embryo is allowed to develop in the uterus until a chosen time, and then the embryo (or fetus) is removed using standard surgical methods to determine its health and viability. Embryos from one species may be placed into the uterine environment of an animal from another species. For example, bovine embryos can develop in the oviducts of sheep (Stice and Keefer, Biology of Reproduction 48: 715–719, 1993). Any cross-species relationship between embryo and uterus may be used in the methods of the invention.

Lipofusion of Nuclei with Oocytes or Other Recipient Cells

The lipofusion solution is prepared by mixing one or more fusigenic reagents with lipofusion buffer in respective proportions ranging from approximately 5:1 to 1:10, as described above. Nuclei, either freshly prepared or frozen and thawed as described above, are mixed with the lipofusion solution to allow coating of the nuclei with the compound. Incubation takes place at a temperature of 20–30° C. for a period of approximately 10–30 minutes. Microdrops containing nuclei in the lipofusion solution are placed under $CO_2$ equilibrated mineral oil. A drop containing the recipient cell, preferably an enucleated cell, is also prepared. Enucleated recipient cells are prepared by physically removing the chromosomes or the nucleus by micromanipulation or by damaging the genetic material by exposure to UV light, as described above. For insertion into oocytes, the nuclei coated with the lipofusion reagent are picked up in a micropipette and inserted in the perivitellin space, between the oocyte cytoplasm and the zona pellucida. For insertion into other recipient cells, the coated nuclei are preferably placed next to the cell membrane to ensure contact with the cell. The nucleus-cell complexes are maintained at a temperature of 20–30° C., and fusion is monitored using a microscope. Once fusion has occurred, reconstituted oocytes are activated as described above.

EXAMPLE 3

Use of Reprogrammed Permeabilized Cells to Clone Mammals

Cells may also be reprogrammed without requiring the isolation of nuclei or chromatin masses from the cells. In this method, cells are permeabilized and then incubated in an interphase or mitotic reprogramming media under conditions that allow the exchange of factors between the media (e.g., a cell extract) and the cells. If an interphase media is used, the nuclei in the cells remain membrane-bounded; if a mitotic media is used, nuclear envelope breakdown and chromatin condensation may occur. After the nuclei are reprogrammed by incubation in this media, the plasma membrane is preferably resealed, forming an intact reprogrammed cell that contains desired factors from the media. If desired, the media can be enriched with additional nuclear factors as described in Example 2. The reprogrammed cells are then fused with recipient oocytes, and embryos formed from the reconstituted oocytes are inserted into maternal recipient mammals for the generation of cloned mammals.

Permeabilization of Cells

Cells that may be reprogrammed using this procedure include unsynchronized cells and cells synchronized in $G_0$, $G_1$, S, $G_2$, or M phase or a combination of these phases. The cells are permeabilized using any standard procedure, such as permeabilization with digitonin or Streptolysin O. Briefly, cells are harvested using standard procedures and washed with PBS. For digitonin permeabilization, cells are resuspended in culture medium containing digitonin at a concentration of approximately 0.001–0.1% and incubated on ice for 10 minutes. For permeabilization with Streptolysin 0, cells are incubated in Streptolysin O solution (see, for example, Maghazachi et al., FASEB J. 11:765–74, 1997, and references therein;) for ~15, 30, or 60 minutes at room temperature. After either incubation, the cells are washed by centrifugation at 400×g for 10 minutes. This washing step is repeated twice by resuspension and sedimentation in PBS. Cells are kept in PBS at room temperature until use. Preferably, the permeabilized cells are immediately added to the interphase or mitotic media for reprogramming, as described below.

Preparation of the Reprogramming Media

To prepare an interphase reprogramming extract, interphase cultured cells are harvested using standard methods and washed by centrifugation at 500×g for 10 minutes in a 10 ml conical tube at 4° C. The supernatant is discarded, and the cell pellet is resuspended in a total volume of 50 ml of cold PBS. The cells are centrifuged at 500×g for 10 minutes at 4° C. This washing step is repeated, and the cell pellet is resuspended in approximately 20 volumes of ice-cold interphase cell lysis buffer (20 mM HEPES, pH 8.2, 5 mM $MgCl_2$, 1 mM DTT, 10 µM aprotinin, 10 µM leupeptin, 10 µM pepstatin A, 10 µM soybean trypsin inhibitor, 100 µM PMSF, and optionally 20 µg/ml cytochalasin B). The cells are sedimented by centrifugation at 800×g for 10 minutes at 4° C. The supernatant is discarded, and the cell pellet is carefully resuspended in no more than one volume of interphase cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract.

The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 µl pipette tip, and the supernatant from several tubes is pooled and placed on ice. This supernatant is the "interphase cytoplasmic" or "ISi5" extract. This cell extract may be aliquoted into 20 µl volumes of extract per tube on ice and immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the IS 15 extract. At the end of centrifugation, the oil is discarded. The supernatant is carefully collected, pooled if necessary, and placed in a cold 1.5 ml tube on ice. This supernatant is referred to as "IS200" or "interphase cytosolic" extract. The extract is aliquoted and frozen as described for the IS 15 extract.

If desired, the extract can be enriched with additional nuclear factors. For example, nuclei can be purified from cells of the cell type from which the reprogramming extract is derived or from cells of any other cell type and lysed by sonication as described above. The nuclear factors are extracted by a 10–60 minute incubation in nuclear buffer containing NaCl or KCl at a concentration of 0.15–800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the cells for reprogramming.

Interphase extracts can also be prepared from germ cells, such as oocytes or male germ cells. For example, oocytes are activated as described above and cultured for five hours to allow entry into interphase. Oocytes are then treated as described in Example 2 for metaphase II oocyte extracts except that EDTA is omitted from the lysis buffer. Male germ cell extracts can be prepared as described in Example 2.

As an alternative to a cell extract, a reprogramming media can also be formed by adding one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) to a solution, such as a buffer. Preferably, one or more of the factors are specific for oocytes or stem cells.

Reprogramming of Cells in a Media

The permeabilized cells are suspended in an interphase reprogramming media described above or one of the mitotic reprogramming medias described in Example 2 at a concentration of approximately 100–1,000 cells/µl. The ATP generating system and GTP are added to the extract as described above, and the reaction is incubated at 30–37° C. for up to two hours to promote translocation of factors from the extract into the cell and active nuclear uptake or chromosome-binding of factors. The reprogrammed cells are centrifuged at 800×g, washed by resuspension, and centrifuged at 400×g in PBS. The cells are resuspended in culture medium containing 20–30% fetal calf serum (FCS), RPMI1640 containing 2 mM $CaCl_2$ (added from a 1 M stock in $H_2O$), or in α-MEM medium containing 2 mM $CaCl_2$ and incubated for 1–3 hours at 37° C. in a regular cell culture incubator to allow resealing of the cell membrane. The cells are then washed in regular warm culture medium (10% FCS) and cultured further using standard culturing conditions.

Alternative Method of Reprogramming Permeabilized Cells on Coverslips Instead of In Solution Alternatively, the cells can be permeabilized while placed on coverslips to minimize the handling of the cells and to eliminate the centrifugation of the cells, thereby maximizing the viability of the cells. Cells (e.g., fibroblasts) are grown on 16-mm poly-L-lysine-coated coverslips in RPM11640 to 50,000–100,000 cells/coverslip in 12-well plates. Cells are permeabilized in 200 ng/ml Streptolysin O in $Ca^{2+}$-free Hanks Balanced Salt Solution (Gibco-BRL) for 50 minutes at 37° C. in regular atmosphere. If desired, the percent of cells that are permeabilized under these conditions can be measured based on propidium iodide uptake. Streptolysin O is aspirated; coverslips are overlaid with 80–100 µl of reprogramming media; and the cells are incubated for thirty minutes to one hour at 37 ° C. in $CO_2$ atmosphere. The reprogramming media preferably contains the ATP generating system and 1 mM each of ATP, CTP, GTP and UTP. To reseal plasma membranes, α-MEM medium containing 2 mM $CaCl_2$, medium containing 20–30% fetal calf serum, or RPMI1640 containing 2 mM $CaCl_2$ is added to the wells, and the cells are incubated for two hours at 37 ° C.

Effect of Various Streptolysin O Treatments on the Percentage of Permeabilized and Resealed Cells To assess the percent of permeabilized and resealed cells, dose and time titrations of Streptolysin O incubation were performed (Table 1). Permeabilization of cells was assessed by uptake of 0.1 µg/ml of the DNA stain propidium iodide at the end of Streptolysin O treatment. Resealing was assessed similarly at the end of the resealing treatment in a separate group of cells.

TABLE 1

Permeabilization and resealing of Streptolysin O (SLO)-treated bovine fibroblasts

| | Permeabilization | | Resealing | |
|---|---|---|---|---|
| ng/ml SLO | N | % pemeabilized +/− sd | N | % Resealed +/− sd |
| 0 | 563 | 1 +/− 2.8 | 560 | 89.9 +/− 4.9 |
| 100 | 404 | 48.6 +/− 4.2 | 810 | 86.1 +/− 8.3 |
| 200 | 548 | 79.2 +/− 1.4 | 478 | 84.9 +/− 1.5 |
| 500 | 495 | 88.7 +/− 1.6 | 526 | 87.6 +/− 0.5 |
| 1000 | 425 | 84.9 +/− 0.7 | 544 | 86.4 +/− 1.4 |
| 2000 | 315 | 96.6 +/− 2.2 | 425 | 10.7 +/− 1 |
| 4000 | 200 | 99 +/− 1.4 | 200 | 11.2 +/− 5.3 |

Assessment of Viability of Bovine Fibroblasts Permeabilized with Streptolysin O Treatment and Exposed to Mitotic Extract TUNEL analysis was performed to evaluate apoptosis in cells permeabilized with 0 or 500 ng/ml Streptolysin O and resealed, or in cells permeabilized with Streptolysin O, exposed to mitotic extract for 30 or 60 minutes, and resealed. TUNEL-positive cells are cells undergoing apoptosis (i.e., cell death). The data show that Streptolysin O itself does not induce apoptosis (Table 2). Exposure of Streptolysin 0-treated cells to the mitotic extract for 60 minutes, but not 30 minutes, induces a 10% increase in apoptotic rate, based on TUNEL analysis (Table 2). Based on these data, a 30-minute incubation of donor cells in the extract is more preferable than a 60 minute incubation. Thirty minute incubations were shown by immunofluorescence analysis of cells to induce nuclear envelope breakdown in the majority of nuclei examined (~90%, n>100).

Additionally, purified nuclei incubated in extract and washed in either buffer N or TL-HEPES and sucrose as described in Example 4 for the chromatin transfer method do not undergo apoptosis (2/34 and 3/47 TUNEL positive, respectively).

TABLE 2

TUNEL analysis of Streptolysin O and Streptolysin O plus extract-treated bovine fibroblasts

| ng/ml SLO | N | % TUNEL pos. +/− sd |
|---|---|---|
| 0 − Input cells | 400 | 7.7 +/− 1.7 |
| 0 | 800 | 6.5 +/− 0.17 |
| 500 | 892 | 7.3 +/− 3.41 |
| 0 + extract 30' | 400 | 5.5 +/− 1.12 |
| 500 + extract 30' | 400 | 8.2 +/− 1.1 |
| 0 + extract 60' | 784 | 6.5 +/− 4.0 |
| 500 + extract 60' | 691 | 16.9 +/− 1.9 |

The permeabilization method chosen for these cloning methods was 500 ng/ml SLO for 30 minutes at 38° C. The resealing method chosen for forming an intact membrane surrounding the reprogrammed cells was a two hour incubation in α-MEM medium containing 2 mM $CaCl_2$.

Formation, Activation, Culturing, and Transplantation of Reconstituted Oocytes

The reprogrammed cells are inserted into, or fused with, recipient oocytes using standard microinjection or electrofusion techniques (see, for example, U.S. Pat. Nos. 4,994, 384 and 5,945,577). For example, the cells can be placed next to the oocytes in standard cell medium in the presence or absence of sucrose (e.g., 2.5 % sucrose), and the cells can be drawn into an injection pippette. The pipette is then aspirated a few times to lyse the cells and remove cytoplasmic components from the nucleus which is then injected into the oocyte. The reconstituted oocytes are then activated, cultured, and transplanted into maternal recipient mammals using standard methods such as those described in Example 2 to produce cloned mammals.

EXAMPLE 4

Evidence for More Complete Nuclear Reprogramming Using Two Novel Cloning Procedures: Chromatin Transfer (CT) and Streptolysin O-transfer (SLOT)

As illustrated Example 1, incomplete nuclear remodeling and reprogramming occurs in traditional nuclear transplant pronuclear stage embryos. This finding was demonstrated by the assembly of lamins A/C in the nuclear envelope of pronuclear nuclear transplant embryos and excess NuMA immunofluorescence labeling. More complete nuclear reprogramming was achieved using the chromatin mass transfer method described in Example 2 and the cell permeabilization and reprogramming method (also referred to as SLOT) described in Example 3.

Figure 5:
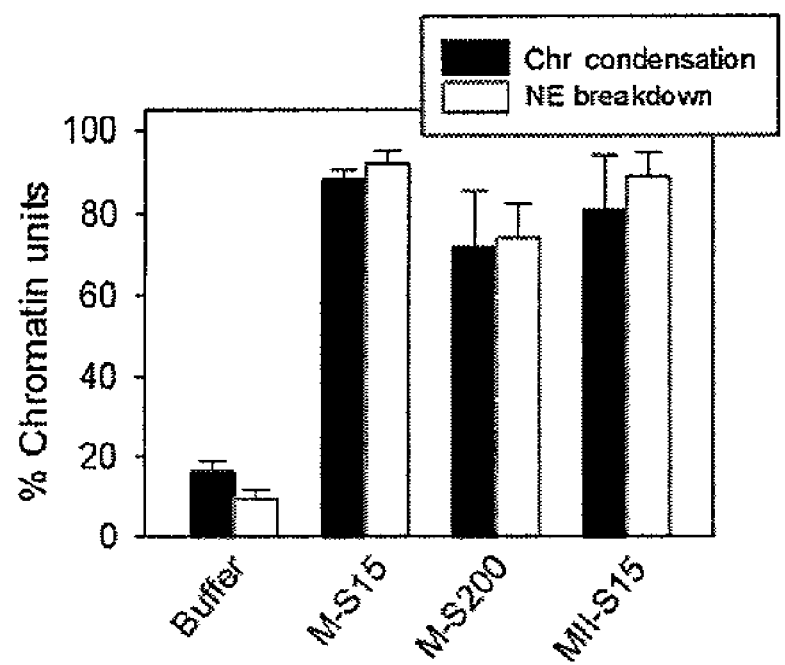
FIG. 5 is a graph of chromosome condensation and nuclear envelope breakdown in mitotic cytoplasmic extract (M-S 15), mitotic cytosolic extract (M-S200), and oocyte extract (MII-S15) (n=300–400 nuclei examined in 3–5 replicates).

Assessment of In Vitro Nuclear Breakdown of Bovine Fibroblast Nuclei Incubated in a Mitotic Extract and Characterization of the Resulting Chromatin Masses Extracts prepared from mitotic bovine fibroblasts consistently supported breakdown of ~80% of input purified fibroblast nuclei (FIG. 5). An extract from metaphase II oocytes (i.e., an extract from oocytes naturally arrested in metaphase II prior to fertilization) also successfully supported nuclear breakdown (75% of nuclei within 30 minutes).

Figures 6A, 6B, 6C:
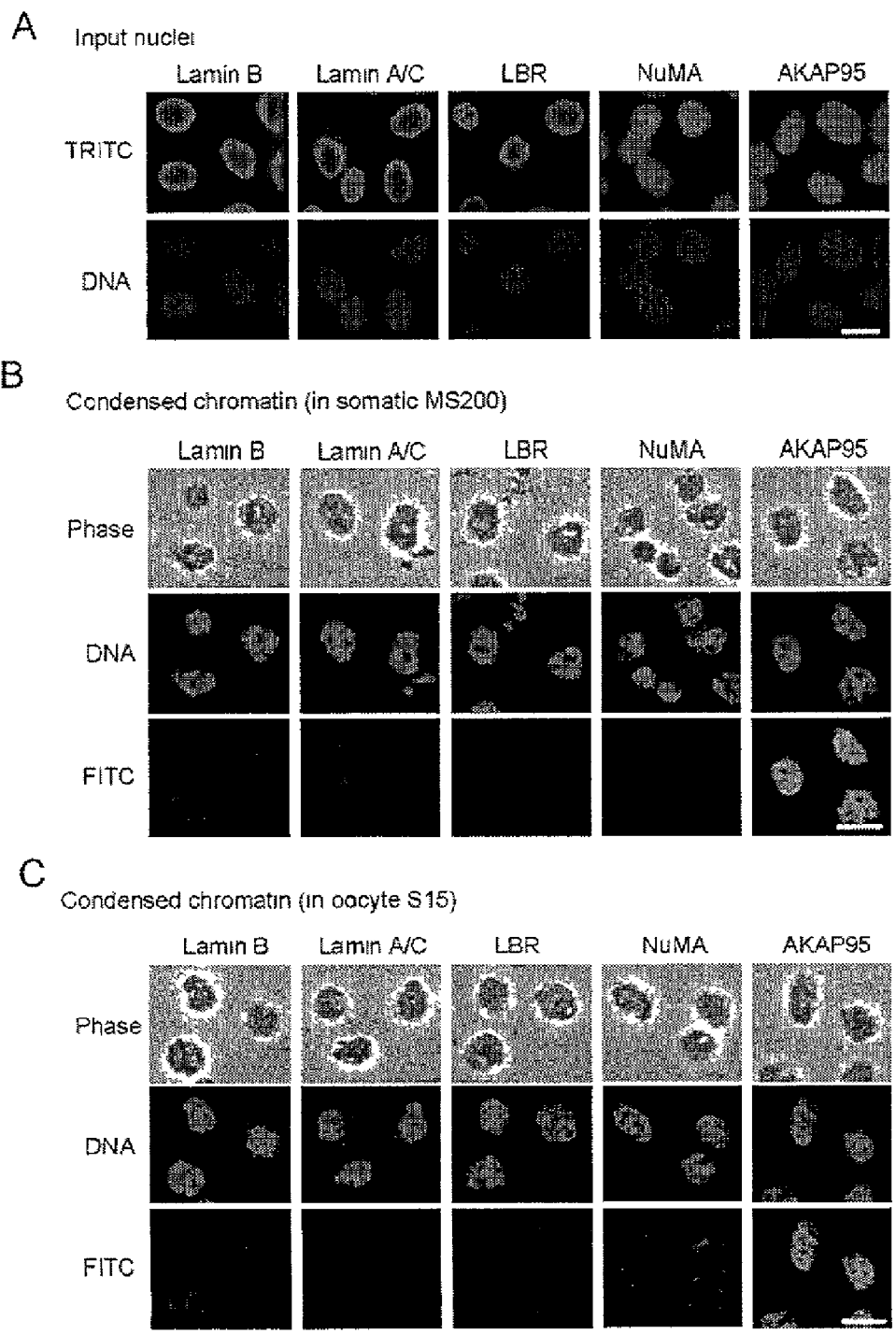
FIGS. 6A–6C are sets of pictures of immunofluorescence analysis of purified input bovine fibroblast nuclei (FIG. 6A) and condensed chromatin produced in mitotic cytosolic extract (FIG. 6B) and oocyte extract (FIG. 6C). The indicated nuclear markers were examined. DNA was counterstained with propidium iodide (red) (bars, 10 μm).
Figure 7:
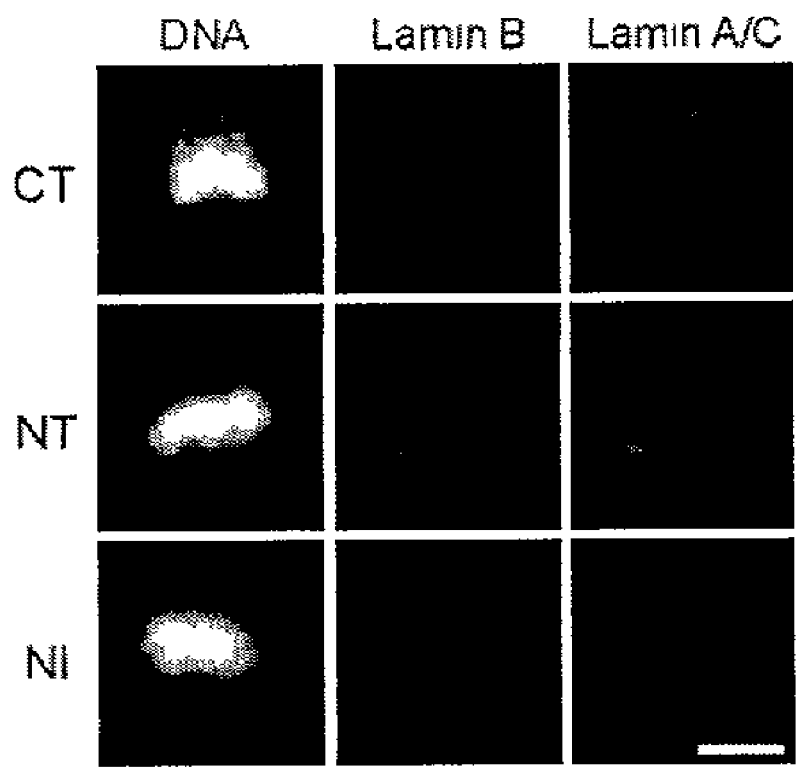
FIG. 7 is a set of pictures of immunofluorescence analysis of condensed chromatin obtained in oocytes following conventional nuclear transplant (NT) or nuclear injection (NI) methods and following injection of chromatin masses into oocytes (CT) using the methods of the present invention. Both detectable lamins B and A/C appear to be solubilized (bar, 10 μm).

Input interphase nuclei (FIG. 6A), chromatin masses obtained from nuclei incubated in a MS15 mitotic extract (FIG. 6B), and chromatin masses obtained from nuclei incubated in an oocyte extract (FIG. 6C) were examined for the expression of the following markers: lamin B receptor (LBR), an integral protein of the inner nuclear membrane (membrane marker); lamin B, a ubiquitous component of the nuclear lamina; lamins A/C, a somatic-specific component of the nuclear lamina present only in differentiated cells and absent in embryos; NuMA, a main component of the nuclear matrix; AKAP95, a PKA-anchoring protein of the nucleus; and DNA. Both somatic cytosolic MS 15 and oocyte MS 15 extracts induced solubilization of lamin B, lamins A/C, LBR, and NuMA in ~100% of chromatin units examined (FIGS. 6B and 6C). As expected, AKAP95 remained associated with chromosomes, as observed previously in mitotic human cells (Collas et al., J. Cell Biol. 147:1167–1180, 1999). This result was also described in Example 1 for bovine nuclear transplant embryos at the premature chromatin condensation stage. Both the mitotic extract and the oocyte extract appeared to be as efficient as intact oocytes in promoting nuclear envelope solubilization, regardless of the method used, i.e., traditional nuclear transplant, nuclear injection (N), or chromatin transfer (FIG. 7).

Comparison of Pronuclear Embryos Produced by Chromatin Transfer and Pronuclei from Nuclear Transplant and Nuclear Injection Embryos To generate chromatin transfer embryos, in vitro-matured oocytes were enucleated about 18–20 hours post maturation. Nuclei from interphase bovine fetal fibroblasts were incubated in a MS 15 mitotic extract that was prepared from bovine fetal cells as described herein. Chromatin masses were isolated from the extract when after nuclear envelope breakdown had occurred and before chromatin condensation was completed. In particular, the chromatin masses were isolated when the chromatin was approximately 50–60% condensed, compared to the level of condensation of chromosomes in interphase (designated 0% condensed) and the maximum level of condensation of chromosomes in mitotsis (designated 100% condensed.) At this stage, individual chromosomes in the chromatin mass could not be distinguished and the edges of the chromatin mass had an irregular shape. Chromatin masses that had been isolated from the mitotic extract were placed in a microdrop of TL HEPES with 2.5% sucrose along with enucleated oocytes. The sucrose was added to the buffer to minimize damage to the ooctyes from the subsequent injection procedure. Chromatin masses were injected into the oocytes using a beveled microinjection pipette using a Burleigh Piezo Drill (Fishers, N.Y.) (frequency 2 Hz for 75 microseconds at an amplitude of 70 V). Typically multiple pulses, such as 2, 3, 4, or 5 pulses, were performed so that the needle sufficiently penetrated the oocyte for injection. After injection, oocytes were washed in serial dilutions of TL HEPES in sucrose to minimize osmotic shock. At 28–30 hours post maturation (i.e., 28–30 hours after oocytes were placed in maturation medium after collection from ovaries, which is also at least two hours after injection of chromatin masses), reconstructed oocytes and controls for parthenogenetic development were activated with calcium ionophore (5 µM) for four minutes (Cal Biochem, San Diego, Calif.) and 10 µg/ml cycloheximide and 2.5 µg/ml cytochalasin D (Sigma) in ACM culture medium [100 mM NaCl, 3 mM KCl, 0.27 mM $CaCl_2$, 25 mM $NaHCO_3$, 1 mM sodium lactate, 0.4 mM pyruvate, 1 mM L-glutamine, 3 mg/ml BSA (fatty acid free), 1% BME amino acids, and 1% MEM nonessential amino acids (Sigma)], for five hours as described earlier (Liu et al., Mol. Reprod. Dev. 49:298–307, 1998). After activation, eggs were washed five times and placed in culture in four-well tissue culture plates containing mouse fetal fibroblasts and 0.5 ml of embryo culture medium covered with 0.3 ml of embryo tested mineral oil (Sigma). Between 25 and 50 embryos were placed in each well and incubated at 38.5° C. in a 5% $CO_2$ air atmosphere. If desired, calcium (e.g., ~0.5, 1.0, 1.5 , 2.0, 2.5, 3, 3.5, 5 mM, or more $CaCl_2$) can be added to the culture medium for ~0.5, 1.0, 1.5, 2.0, 2.5, 3.0, or more hours to promote resealing of the oocyte after injection. The resealed oocytes are likely to have increased survival rates due to the intact layer surrounding the oocytes when they are implanted into the recipient mammal using the standard methods described herein.

Nuclear injection embryos were formed as described above for chromatin transfer embryos, except that interphase bovine fetal fibroblasts nuclei that had not been incubated in an extract were injected into the oocytes instead of chromatin masses. Nuclear transplant embryos were generated using the conventional methods described in Example 1.

Figure 8A:
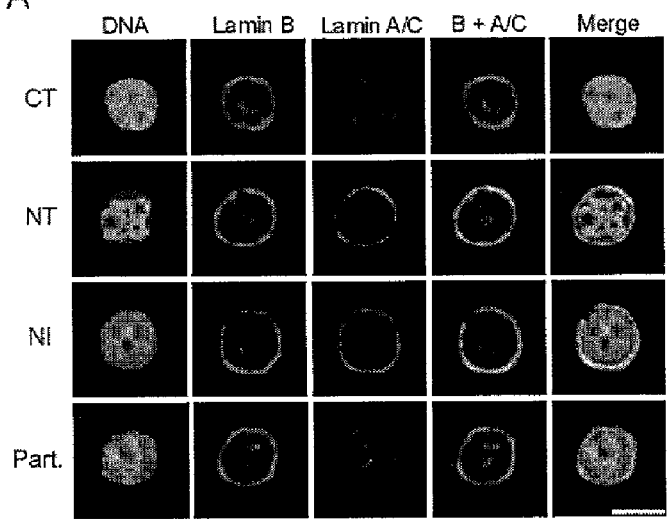
FIGS. 8A and 8B are sets of pictures of immunofluorescence analysis of pronuclei resulting from chromatin transfer, nuclear transplant, or nuclear injection. Embryos were fixed at 19 hours post nuclear transplant, nuclear injection, or chromatin transfer and labeled. Control parthenogenetic pronuclei (Part.) were also examined.
Figure 8B:
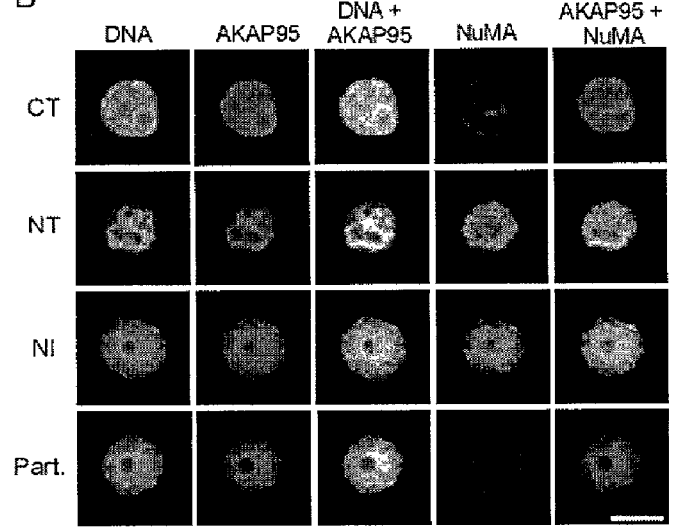

Nuclear transplant, nuclear injection, and chromatin transfer pronuclei reassemble lamin B (FIG. 8A, red label) and AKAP95 (FIG. 8B, red label) as anticipated. Nuclear transplant and nuclear injection pronuclei also reassemble lamins A/C, a somatic-specific component (FIG. 8A, green label), consistent with the results reported above for nuclear transplant embryos. However, chromatin transfer pronuclei and control parthenote pronuclei do not reassemble lamins A/C (FIG. 8A). Nuclear transplant pronuclei also contain NuMA (green label), unlike most chromatin transfer or parthenote pronuclei (FIG. 8B, green label). A proportion of parthenote nuclei and chromatin transfer nuclei assemble a low level of NuMA, as reported above.

In vitro disassembly of nuclei followed by chromatin transfer results in pronuclei that are morphologically similar to control parthenote pronuclei. In contrast, nuclear transplant and nuclear injection pronuclei harbor somatic-specific components (lamins A/C and extensive NuMA labeling). This result is indicative of incomplete nuclear remodeling after traditional nuclear transplant or nuclear injection procedures. As described above, lamins A/C detected in nuclear transplant and nuclear injection pronuclei originate from lamins transcribed de novo at the pronuclear stage. Because nuclear lamins and possibly NuMA are implicated in transcription regulation and disease in humans, persistence of lamins A/C in conventional nuclear transplant pronuclei might be indicative of improper functional reprogramming. We conclude that in vitro nuclear disassembly and chromatin transfer produces more normal pronuclei than traditional nuclear transplant or nuclear injection.

Cloning Efficiency Using Reprogrammed Chromatin Masses or Permeabilized Cells as Donor Source As described in Example 3, a novel cloning procedure denoted "SLOT" was developed that involves Streptolysin O (SLO)-induced permeabilization of primary fetal bovine fibroblasts, exposure of permeabilized cells to a reprogramming media (e.g., a mitotic extract) for 30 minutes, resealing of the fibroblasts with 2 mM calcium in culture, and transfer of the chromatin into oocytes using standard cell fusion methods.

For this cloning method, a vial of Streptolysin O (Sigma S-5265; 25,000 units stored in store powder form at 4° C.) was dissolved in 400 µl H$_2$O and mixed well. All contents were transferred to a 15-ml conical tube, and then 3.6 ml H$_2$O was added and mixed by vortexing. Aliquots of 10 µl were frozen at ~20° C. at a stock concentration of 0.062 U/µl. Cells (~100,000) were suspended in 100 µl HBSS (Gibco BRL, cat. No. 14170–120) at room temperature. These cells were confluent, and thus ~80–85% of the cells were in G1 phase, and the majority of the other cells were in S phase. Streptolysin O stock solution (5 µl) (i.e., 500 ng/ml or 0.3 U/µl final concentration) was added, and the mixture was incubated at 38° C. for 25 minutes in a water bath. The tube was gently tapped 2–3 times during incubation to ensure that the cells remained in suspension. Room temperature PBS (200 µl) was added and mixed well by gentle pipetting. The cells were centrifuged cells at 5,000 rpm for five minutes at room temperature in a table top centrifuge. All the supernatant was discarded. At this stage, the pellet is small and may not be clearly visible. Mitotic extract containing the ATP-generating system (40 µl, "MS15") was added and mixed well. The extract was prepared during the centrifugation of the cells by thawing one vial of 40 µl extract and adding 1.2 µl of ATP-generating system, mixing well, and incubating at room temperature. This mitotic extract was the same extract used for the generation of chromatin masses in the section above. The mixture was incubated at 38° C. in water bath for 30 minutes, and the tube was occasionally gently tapped. Room temperature resealing medium (RM, 500 µL) (complete α-MEM [Bio-Whittaker] medium supplemented with CaCl$_2$ to 2 mM from a 1 M stock) was added. The tube was left open and incubated in a CO$_2$ incubator for two hours with occasional tapping of the tube to ensure that the cells remained in suspension. The cells were centrifuged at 5,000 rpm for five minutes at room temperature in a table top centrifuge. The cell pellet was resuspended in 100 µl of room temperature TL HEPES (Bio-Whittaker, cat. No. 04–616F), and another 900 µl TL HEPES was added. The nuclear transfer was performed using standard procedures. Oocytes were activated and transferred to recipient mammals as described in the previous section for chromatin transfer.

The development of embryos formed using this SLOT method and the chromatin transfer method of the present invention is summarized in Table 3. Development to the blastocyst stage was slightly lower for SLOT embryos compared to conventional nuclear transfer embryos. The differences between SLOT and nuclear transfer development at the blastocyst stage could be due to the effect of using a greater precentage of cells in the G1 phase of the cell cycle for nuclear transfer than for SLOT. The survival rate was lower for chromatin transfer embryos, which is expected for an invasive procedure.

Pregnancy rates were comparable for nuclear transfer and SLOT embryos at 40 days of gestation (Table 3). Survival from 40 days of pregnancy to 60 days tended to be higher for SLOT embryos than for nuclear transfer embryos produced using conventional methods.

TABLE 3

Development of chromatin transfer (CT), nuclear transplant, and SLOT-produced bovine embryo clones

| | No. transferred | No. Survived (%) | No. PN stage (%) | No. Cleaved (%) | No. Blastocysts (%) | No. 40 day Preg. (%) | No. Survived 40–60 days/total (%) |
|---|---|---|---|---|---|---|---|
| CT | 1503 | 736 (49) | 355 (23.5) | 81 (5.3) | 3 | 0 | ND |
| SLOT | 1884 | 1802 (97) | ND | 575 (30.5) | 156 (8.3) | 24/65 (37) | 7/10 (70) |
| nuclear transplant | 1821 | 1682 (92) | ND | 764 (41.9) | 235 (12.9) | 39/103 (36) | 8/16 (50) |

As noted above, the survival rate for chromatin transfer embryos may be increased by incubating the reconstituted oocytes in calcium for a few hours to allow the oocytes to reseal prior to be inserted into recipient mammals. Survival rates for SLOT embryos may also be increased by reducing the amount of time between when the cells are taken out of culture and when they are fused with oocytes. For example, the length of time for the incubation in Streptolysin 0, the incubation in the reprogramming medium, and/or the incubation in the resealing medium may be decreased. In particular, the incubation in the resealing medium may be decreased to approximately one hour or less. This shortened resealing treatment may be performed in the presence of 2 mM calcium as described above or in the presence of a higher concentration of calcium (e.g., ~2.5, 3.0, 3.5, 4.0, 4.5, 5.0, or 6.0 mM calcium) to increase the rate of resealing. By reducing the amount of time the cells are treated prior to being fused with oocytes, the cells are less likely to enter S phase and begin DNA replication which reduces the survival rate of the reconstituted oocyte.

EXAMPLE 5

Methods for the Generation of Chimeric Mammals

Many spontaneous abortions that occur using traditional methods to clone mammals are thought to result from placental abnormalities rather than from problems with the fetus. Thus, methods have been developed to produce chimeric embryos with placental tissue primarily from one origin (e.g., an in vitro fertilized, naturally-occurring, or parthenogenetically activated embryo) and fetal tissue primarily from another origin (e.g., a nuclear transfer embryo). Chimeric embryos with placental tissue derived primarily from cells from in vitro fertilized, naturally-occurring, or parthenogenetically activated embryos may better resemble naturally-occurring placental tissue and result in increased production of viable offspring. Preferably, the majority of the cells of the offspring are derived from cells from the nuclear transfer embryo and thus have a genome that is substantially identical to that of the donor cell used to generate the nuclear transfer embryo.

In one such method, cells from an in vitro fertilized embryo are injected into the periphery of a compaction embryo (e.g., between the zona pellucida and the embryo itself) that was produced using traditional nuclear transfer methods or any of the novel cloning methods described herein. In an alternative method, cells from a precompaction, in vitro fertilized embryo are incubated with cells from a precompaction embryo produced using one of the cloning methods of the present invention (e.g., using a reprogrammed chromatin mass or a permeabilized cell as the donor source) under conditions that allow cells from each embryo to reorganize to produce a single chimeric embryo (Wells and Powell, Cloning 2:9–22, 2000). In both methods, the cells from the in vitro fertilized embryo are preferentially incorporated into the placenta, and the cells from the nuclear transfer method are preferentially incorporated into the fetal tissue. These methods are described further below.

Isolation of G1 Fibroblasts

For the isolation of G1 fibroblasts as donor cells to produce nuclear transfer embryos, the previously described "shake off" method was used (Kasinathan et al., Nature biotech. 19:1176–1178, 2001). Briefly, 24 hours prior to isolation, $5.0 \times 10^5$ cells were plated onto 100 mm tissue culture plates containing 10 ml of α-MEM plus FCS. The following day, plates were washed with PBS, and the culture medium was replaced for one to two hours before isolation. The plates were then shaken for 30–60 seconds on a Vortex-Genie 2 (Fisher Scientific, Houston, Tex., medium speed). The medium was removed, spun at 500×g for five minutes, and the pellet was re-suspended in 250 μl of MEM plus FCS. This cell suspension consisted of newly divided cell doublets attached by a cytoplasmic bridge, some single cells, and metaphase or anaphase cells. The cell doublets attached by a cytoplasmic bridge were used as donor cells for nuclear transfer.

Nuclear Transplantation, Activation and Embryo Culture

The nuclear transfer procedure using the isolated G1 fibroblasts was performed essentially as previously described (Cibelli et al., Nature Biotech. 16(7):642–646, 1998; Kasinathan et al., Biol. Reprod. 64(5):1487–1493, 2000). In vitro matured oocytes were enucleated about 18–20 hours post maturation, and chromosome removal was confirmed by bisBenzimide (Hoechst 33342, Sigma) labeling under UV light. These cytoplast-donor cell couplets were fused using a single electrical pulse of 2.4 kV/cm for 20 mircoseconds (Electrocell manipulator 200, Genetronics, San Diego, Calif.). At 30 hours past maturation, reconstructed oocytes and controls were activated with calcium ionophore (5 μM) for four minutes (Cal Biochem, San Diego, Calif.) and 10 μg cycloheximide and 2.5 μg cytochalasin D (Sigma) in ACM culture medium (100 mM NaCl, 3 mM KCl, 0.27 Mm $CaCl_2$, 25 mM $NaHCO_3$, 1 mM sodium lactate, 0.4 mM Pyruvate, 1 mM L-glutamine, 3 mg/ml BSA (fatty acid free), 1% BME amino acids, and 1% MEM nonessential amino acids; all from Sigma) for six hours as described previously (Liu et al., Mol. Reprod. Dev. 49:298–307, 1998; Presicce et al., Mol. Reprod. Dev. 38:380–385, 1994). After activation, eggs were washed in HEPES buffered hamster embryo culture medium (HECM-HEPES, 114 mM NaCl, 3.2 mM KCl, 2 mM $CaCl_2$, 10 mM Sodium Lactate, 0.1 mM sodium pyruvate, 2 mM $NaHCO_3$, 10 mM HEPES, and 1% BME amino acids; Sigma) five times and placed in culture in 4-well tissue culture plates containing mouse fetal fibroblasts and 0.5 ml of embryo culture medium covered with 0.2 ml of embryo tested mineral oil (Sigma). Twenty five to 50 embryos were placed in each well and incubated at 38.5 C. in a 5 % $CO_2$ in air atmosphere. On day four, 10% FCS was added to the culture medium. On days seven and eight, development to the blastocyst stage was recorded.

Bovine In vitro Fertilization

In vitro fertilization was performed as described earlier to produce bovine in vitro fertilized embryos (Collas et al., Mol. Reprod. Dev. 34:224–231, 1993). A 45% and 90% isotonic Percoll gradient was prepared with sperm TL stock (Parrish et al., Theriogenology 24:537–549, 1985). Frozen-thawed bovine sperm from a single bull was layered on top of the gradient and centrifuged for 30 minutes at 700×g (2000 rpm using a 6.37 inch tip radius). The concentration of sperm in the pellet was determined, and the sperm was diluted in sperm TL (sperm TL stock, 1 mM pyruvate, 6 mg/ml BSA, and 1% PS) such that the final concentration at fertilization was $10^6$ sperm/ml. At 22 hours post maturation, oocytes were wash three times in TL HEPES and placed in 480 ul of fertilization TL (Bavister et al., Biol. Reprod. 28:235–247, 1983) in Nunc wells containing 6 mg/ml BSA, 0.2 mM pyruvate, 20 uM penicillamine, 10 uM hypotaurine, 1 mM epinepherine (Leibfried et al., J. Reprod. Fertil. 66:87–93, 1982), and 0.004 ug/ml heparin. Twenty microliters of sperm were added to generate a final concentration of $10^6$ sperm/ml to 50 oocytes. Culture conditions were the same as those described above for nuclear transfer. Fertilization rates were over 90% based on pronuclear development.

Chimeric Nuclear Transfer Embryos

In vitro fertilized embryos at 8-cell stage (6–12 blastomeres) were harvested at approximately 96 hours post fertilization, prior to compaction. The zona pellucida was removed with protease (3 mg/ml in TL-HEPES). The zona dissolution was carefully monitored using a dissecting microscope. When the zona first appeared to dissolve (~two minutes), the embryos were removed and washed in TL-HEPES and transferred to 30 mm petri dishes containing Hank's balanced salt solution and incubated at 37.5 C. for 30 minutes. The blastomeres from these precompaction embryos were transferred into microdrops (50 μl) of TL-HEPES under mineral oil in 100 mm petridish. Nuclear transfer embryos on day four at the 8–16 cell stage were selected and transferred into the same microdrops containing the blastomeres. These nuclear transfer embryos included both precompaction embryos (e.g. 8 cell stage embryos) and compaction embryos (e.g., 16 stage embryos). Then 4–6 blatomeres were transferred into the nuclear transfer embryos with the beveled micro pipette (35 μm diameter) using standard micromanipulation techniques. After transferring the blastomeres, the embryos were cultured as described for nuclear transfer embryos.

On days seven and eight, the development to blastocyst of the chimeric embryos was evaluated. The blastocysts were also analyzed for the presence of the membrane dye DiI that was added to the cells from the in vitro fertilized embryo before they were injected into the nuclear transfer embryo. The cells were labeled on day four and observed on day seven. This dye is maintained for a few cell divisions in the progeny of the originally dyed cells, allowing the chimeric embryo to be analyzed after a few cell divisions. Based on this analysis, cells from the in vitro fertilized embryo were incorporated into the chimeric embryo. If desired, fluorescence in situ hybridization (FISH) with a probe specific for a nucleic acid in either the in vitro fertilized embryo or the nuclear transfer embryo can be performed using standard methods (see, for example, Ausubel et al., Current Protocols in Molecular Biology, John Wiley & Sons, New York, pp. 14.7.1–14.7.12, 1995). This FISH analysis can be used to determine the distribution of cells derived from each embryo in the chimeric embryo (e.g., to determine what percent of the cells are incorporated into the inner cell mass and what percent are incorporated into the trophectoderm) while it is cultured in vitro and in the fetus or the offspring generated from the embryo. Alternatively, a reporter gene such as green fluorescent protein can be added to cells from one of the embryos and used to monitor the incorporation of the cells into the placenta and various fetal tissues of the chimeric embryo.

Embryo Transfer

Days seven and eight, nuclear transfer blastocysts of grade 1 and 2, derived from nuclear transfer embryos and chimeric nuclear transfer embryos were transferred into day six and seven synchronized recipient heifers. Recipients were synchronized using a single injection of Lutalyse (Parmacia & Upjohn, Kalamazoo, Mich.) followed by estrus detection. The recipients were examined on days 30 and 60 after embryo transfer by ultrasonography for the presence of conceptus and thereafter every 30 days by rectal palpation until 240 days. The pregnancy results at day 40 for the chimeric embryos and for control embryos produced by fusing a transgenic bovine fibroblast with an oocyte are compared in Table 4. These results indicate that a greater number of chimeric embryos survived until day 40.

TABLE 4

Embryo transfers and pregnancies

| Implant | Control Nuclear transfers | | Chimeric Nuclear Transfers | |
|---|---|---|---|---|
| | No of recipients | 40 day Pregnancy | No of recipients | 40 day Pregnancy |
| First | 2 | 1 | 2 | 1 |
| Second | 6 | 1 | 4 | 3 |
| Total | 8 | 2 (25%) | 6 | 4 (67%) |

Alternative Methods for Production of Chimeric Embryos

Standard methods can be used to modify the above method for producing chimeric embryos. For example, a naturally-occurring embryo can be surgically isolated from a mammal (e.g., a bovine) or an oocyte can be parthenogenetically activated using standard techniques and used instead of the in vitro fertilized embryo. If desired, fewer cells from the in vitro fertilized, naturally-occurring, or parthenogenetically activated embryos (e.g., 1, 2, 3, 4, or 5 cells) can be injected into the nuclear transfer embryo to reduce the percent of the injected cells and their progeny that become incorporated into fetal tissue, Alternatively, more cells (e.g., 6, 7, 8, 9, 10, 11 or more cells) can be injected to increase the percent of the injected cells and their progeny that are incorporated into placental tissue. Moreover, cells from embryos in other cell stages can be used. For example, in vitro fertilized, naturally-occurring, or parthenogenetically activated embryos at the 4, 8, 16, 32, 64, 128, 256, 512, or later cell stage can be injected into nuclear transfer embryos at the 4, 8, 16, 32, 64, 128, 256, 512, or later cell stage. The injected cells and the nuclear transfer embryo can be at the same cell stage or at different cell stages. In one embodiment, the in vitro fertilized, naturally-occurring, or parthenogenetically activated embryo has increased ploidy (e.g., a DNA content of 4n) relative to the nuclear transfer embryo, which further biases the injected cells to the trophectoderm (i.e., the outermost layer of cells of the embryo that primarily forms the placental tissue). If desired, all or part of the zona pellucida can be kept surrounding the injected cells, rather than removed prior to injection.

In other alternative methods, cells from a precompaction or compaction in vitro fertilized, naturally-occurring, or parthenote embryo are incubated with cells from a precompaction nuclear transfer embryo under conditions that allow cells from each embryo to reorganize to produce a single chimeric embryo (Wells and Powell, Cloning 2:9–22, 2000). Cells from in vitro fertilized, naturally-occurring, or parthenote embryo are expected to contribute primarily to the trophectoderm and eventually to the placental tissue, and cells from the nuclear transfer embryo are expected to contribute primarily to the inner cell mass and eventually to the fetal tissue. Cells from both embryos can be at the same cell stage or at different cell stages, and the same or different numbers of cells from each embryo can be combined to form the aggregation embryo.

OTHER EMBODIMENTS

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A method of cloning a non-human mammal, said method comprising the steps of:
   (a) permeabilizing a non-human mammalian cell, thereby generating a permeabilized cell having pores in its plasma membrane or a partial plasma membrane;
   (b) incubating said permeabilized cell in an extract from a mitotic cell under conditions that allow chromatin condensation and nuclear envelope breakdown of said permeabilized cell;
   (c) inserting said cell formed in step (b) into a nucleated or enucleated oocyte, thereby forming a reconstituted oocyte; and
   (d) transferring said reconstituted oocyte or an embryo formed from said reconstituted oocyte into the uterus of a host mammal under conditions that allows said reconstituted oocyte or said embryo to develop into a fetus.

2. The method of claim 1, wherein a chromatin mass is formed from incubation of said permeabilized cell in said extract from said mitotic cell.

3. The method of claim 1, wherein, said cell formed in step (b) is incubated under conditions that allow the plasma membrane of said cell to reseal.

4. The method of claim 1, wherein said cell formed in step (b) is purified from said extract from said mitotic cell prior to insertion into said nucleated or enucleated oocyte.

5. The method of claim 1, wherein said fetus develops into a viable offspring.

6. The method of claim 1, wherein said reconstituted oocyte from step (c) is cultured under conditions that allow cell division and one of the resulting cells is recloned one or more times.

7. The method of claim 1, wherein said permeabilized cell and said nucleated or enucleated oocyte are from the same species.

8. The method of claim 1, wherein said non-human mammal is a cow, sheep, rabbit, pig, mouse, rat, goat, or buffalo.

9. The method of claim 8, wherein said non-human mammal is a cow.

10. The method of claim 1, wherein said permeabilized cell is a fibroblast, epithelial cell, neural cell, epidermal cell, keratinocyte, hematopoietic cell, melanocyte, chondrocyte, B-lymphocyte, T-lymphocyte, erythrocyte, macrophage, monocyte, muscle cell, embryonic stem cell, embryonic germ cell, fetal cell, placental cell, or embryonic cell.

11. The method of claim 1, wherein said permeabilized cell is a cell of the female reproductive system.

12. The method of claim 11, wherein said permeabilized cell is a mammary gland, ovarian cumulus, granulosa, or oviductal cell.

13. The method of claim 1, wherein said reconstituted oocyte from step (b) expresses lamin A, lamin C, or NuMA protein at a level that is less than 5-fold greater than the corresponding level expressed by a control oocyte from the same species.

14. The method of claim 1, wherein said extract from said mitotic cell is an extract from a mitotic somatic cell.

15. The method of claim 1, wherein said permeabilized cell is generated by incubating a somatic cell from a non-human mammal with streptolysin O.

16. The method of claim 15, wherein said streptolysin O concentration is between 100–4000 ng/ml.

17. The method of claim 16, wherein said streptolysin O concentrate is 500 ng/ml.

18. The method of claim 15, wherein said incubating with streptolysin O is carried out for 15–60 minutes.

19. The method of claim 18, wherein said incubating with streptolysin O is carried out for between 25–30 minutes.

20. The method of claim 15, wherein said incubating with streptolysin O is carried out at between 25–38° C.

21. The method of claim 20, wherein said incubating with streptolysin O is carried out at 38° C.

22. The method of claim 1, wherein said inserting in step (c) is carried out by fusion of said permeabilized cell with said nucleated or enucleated oocyte.

23. The method of claim 1, wherein said oocyte of step (c) is enucleated.

24. The method of claim 1, wherein said reconstituted oocyte is activated prior to transfer into the uterus of said host mammal.

* * * * *

UNITED STATES PATENT AND TRADEMARK OFFICE
CERTIFICATE OF CORRECTION

PATENT NO. : 7,253,334 B2
APPLICATION NO. : 10/032191
DATED : August 7, 2007
INVENTOR(S) : Collas et al.

It is certified that error appears in the above-identified patent and that said Letters Patent is hereby corrected as shown below:

Title Pg, Item (56) Ref. Cited
On Page 3,
    under OTHER PUBLICATIONS, in Haslet,
        replace "Cattle,"J." with --Cattle, J.--.
    under OTHER PUBLICATIONS, in Kono et al.,
        replace "Chimaeric Two-Cell" with --Chimeric Two Cell--.

Column 1, Line 50, replace "ooctye" with --oocyte--.

Column 4, Line 35, replace "90. 95," with --90, 95,--.

Column 8, Line 3, replace "mule," with --mules,--.

Column 13,
    Line 17, replace "blastomereres" with --blastomeres--.
    Line 20, replace "E-adherin" with --E-cadherin--.

Column 18, Line 47, replace "$10^6$ spenn/ml." with --$10^6$ sperm/ml--.

Column 22, Line 60, replace "b'"in" with --b'" in--.

Column 26, Line 31, replace "1 µI" with --1 µl--.

Column 27,
    Line 55, replace "10 mM MgSO4," with --10 mM $MgSO_4$,--.
    Line 55, replace "ImM EDTA," with --1 mM EDTA,--.
    Line 60, replace "J. Biol. Chem 272:" with --J. Biol. Chem. 272:--.

Column 28, Line 59, replace "enucleatation" with --enucleation--.

Column 32,
    Line 10, replace "ISi5" with --IS15--.
    Line 23, replace "IS 15" with --IS15--.

Column 33,
    Line 15, replace "RPM11640" with --RPMI1640--.
    Line 48, In TABLE 1, under Permeabilization, replace "pemeabilized" with
        --permeabilized--.

UNITED STATES PATENT AND TRADEMARK OFFICE
CERTIFICATE OF CORRECTION

PATENT NO. : 7,253,334 B2
APPLICATION NO. : 10/032191
DATED : August 7, 2007
INVENTOR(S) : Collas et al.

It is certified that error appears in the above-identified patent and that said Letters Patent is hereby corrected as shown below:

Column 34, Line 42, replace "pippette" with --pipette--.

Column 35,
  Line 50, replace "mitotsis" with --mitosis--.
  Line 58, replace "ooctyes" with --oocytes--.

Column 36, Line 29, replace "ooctyes" with --oocytes--.

Column 38, Line 3, replace "precentage" with --percentage--.

Column 39, Line 47, replace "mircoseconds" with --microseconds--.

Column 40,
  Line 22, replace "epinepherine" with --epinephrine--.
  Line 48, replace "blatomeres" with --blastomeres--.

Column 42,
  Line 34, in claim 1, replace "non-human" with --non-primate--.
  Line 36, in claim 1, replace "non-human" with --non-primate--.
  Line 48, in claim 1, replace "allows" with --allow--.

Signed and Sealed this

Tenth Day of February, 2009

JOHN DOLL
*Acting Director of the United States Patent and Trademark Office*